(12) United States Patent
Tosato et al.

(10) Patent No.: US 11,401,544 B2
(45) Date of Patent: Aug. 2, 2022

(54) METHODS OF PREPARING A RE-USABLE SINGLE CELL AND METHODS FOR ANALYZING THE EPIGENOME, TRANSCRIPTOME, AND GENOME OF A SINGLE CELL

(71) Applicant: The United States of America, as represented by the Secretary, Department of Health and Human Services, Bethesda, MD (US)

(72) Inventors: Giovanna Tosato, Bethesda, MD (US); Hidetaka Ohnuki, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 42 days.

(21) Appl. No.: 16/611,098

(22) PCT Filed: May 4, 2018

(86) PCT No.: PCT/US2018/031201
§ 371 (c)(1),
(2) Date: Nov. 5, 2019

(87) PCT Pub. No.: WO2018/204854
PCT Pub. Date: Nov. 8, 2018

(65) Prior Publication Data
US 2020/0102604 A1    Apr. 2, 2020

Related U.S. Application Data

(60) Provisional application No. 62/502,247, filed on May 5, 2017.

(51) Int. Cl.
| | |
|---|---|
| *C12N 1/14* | (2006.01) |
| *C12Q 1/6834* | (2018.01) |
| *C12Q 1/6806* | (2018.01) |
| *C12Q 1/6827* | (2018.01) |
| *C12Q 1/6874* | (2018.01) |
| *B82Y 5/00* | (2011.01) |

(52) U.S. Cl.
CPC ............ *C12Q 1/6834* (2013.01); *C12N 1/14* (2013.01); *C12Q 1/6806* (2013.01); *C12Q 1/6827* (2013.01); *C12Q 1/6874* (2013.01); *B82Y 5/00* (2013.01); *C07K 2317/77* (2013.01); *C12Q 2523/101* (2013.01); *C12Q 2565/518* (2013.01); *C12Q 2565/629* (2013.01); *C12Q 2600/154* (2013.01); *C12Q 2600/156* (2013.01); *C12Q 2600/158* (2013.01)

(58) Field of Classification Search
CPC ..... C08F 220/56; A61L 27/52; C12N 2533/30
See application file for complete search history.

(56) References Cited

U.S. PATENT DOCUMENTS

| | | | |
|---|---|---|---|
| 5,470,722 A | 11/1995 | Jones | |
| 6,368,791 B1 | 4/2002 | Felix et al. | |
| 2015/0104812 A1* | 4/2015 | Grevesse | ............... A61L 27/16 |
| | | | 435/7.21 |
| 2016/0271064 A1 | 9/2016 | Sell et al. | |

FOREIGN PATENT DOCUMENTS

| | | |
|---|---|---|
| CN | 106148159 A | 11/2016 |
| WO | WO 2016/207441 A1 | 12/2016 |

OTHER PUBLICATIONS

Chen et al., "Single-cell analysis at the threshold," *Nat. Biotechnol.*, 34(11): 1111-1118 (2013).
European Patent Office, International Search Report in International Patent Application PCT/US2018/031201 (dated Aug. 30, 2018).
European Patent Office, Written Opinion in International Patent Application PCT/US2018/031201 (dated Aug. 30, 2018).
Johnson et al., "Application of acrylamide as an embedding medium in studies of lectin and antibody binding in the vertebrate retina," *Current Eye Research*, 3(7): 969-974 (1984).
Jones et al., "Targeting the cancer epigenome for therapy," *Nat. Rev. Genetics*, 17(10): 630-641 (2016).
Rotem et al., "Single-cell ChIP-seq reveals cell subpopulations defined by chromatin state," *Nat. Biotechnol.*, 21(10): 2278-88 (2015).
Spits et al., "Whole-genome multiple displacement amplification from single cells," *Nat. Protoc.*, 4: 1965-1970 (2006).
Suzuki et al., "Postembedding Staining of Brunner's Gland with Lectin-Ferritin Conjugates," *Journal of Histochemistry and Cytochemistry*, 29(8): 946-952 (1981).
Toriello et al., "Integrated microfluidic bioprocessor for single-cell gene expression analysis," *Nat. Rev. Genet.*, 17(10): 630-641 (2016).
Word et al., "Improved method of single-cell epigenome analysis," Vanderbilt University, NIH Summer Research Program Poster Day (Aug. 10, 2017).
Xu et al., "Virtual microfluidics for digital quantification and single-cell sequencing," *Nat. Methods*, 13(9):759-762 (Abstract, Aug. 1, 2016).

\* cited by examiner

*Primary Examiner* — Karen Cochrane Carlson
(74) *Attorney, Agent, or Firm* — Leydig, Voit & Mayer, Ltd.

(57) ABSTRACT

Methods and kits for preparing re-usable single cells are described. Cell components are anchored using a nano-scale scaffold to create a re-usable single cell. The nano-scale scaffold may be a polyacrylamide nano-scale scaffold. Methods to determine modifications of the genome, transcriptome, or epigenome are described.

18 Claims, 20 Drawing Sheets

Specification includes a Sequence Listing.

Step 1

Step 2

Step 3

Step 4

Figure 5D

Step 5

Step 6

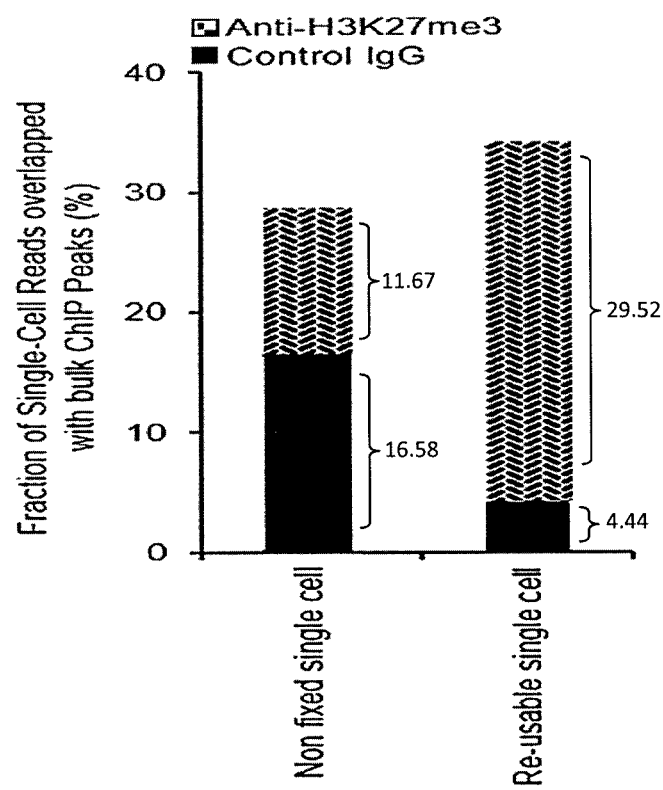
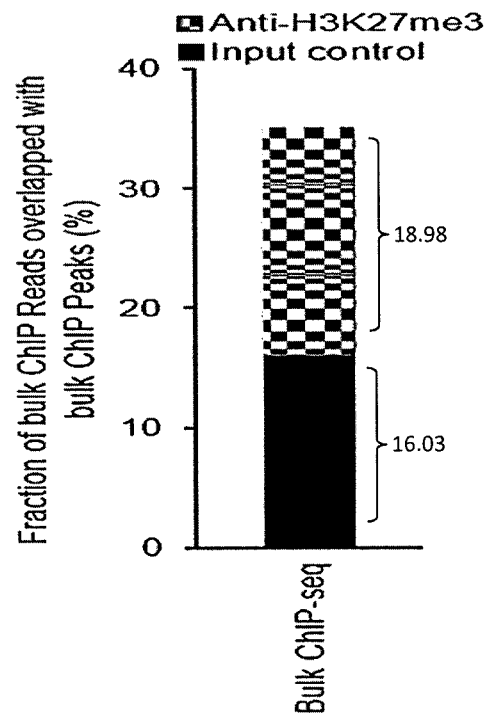
Figure 8B                    Figure 8C

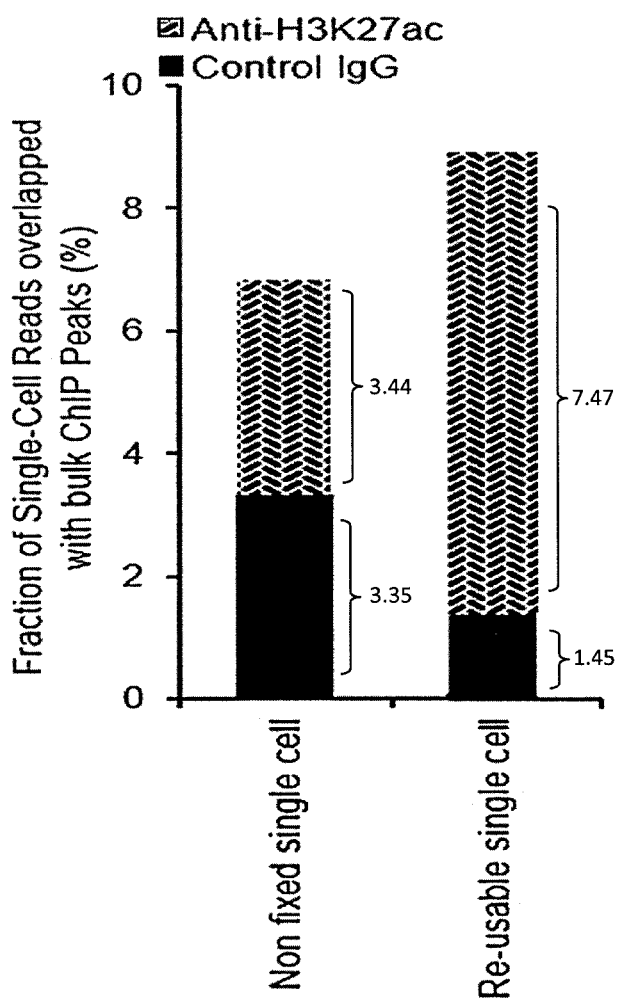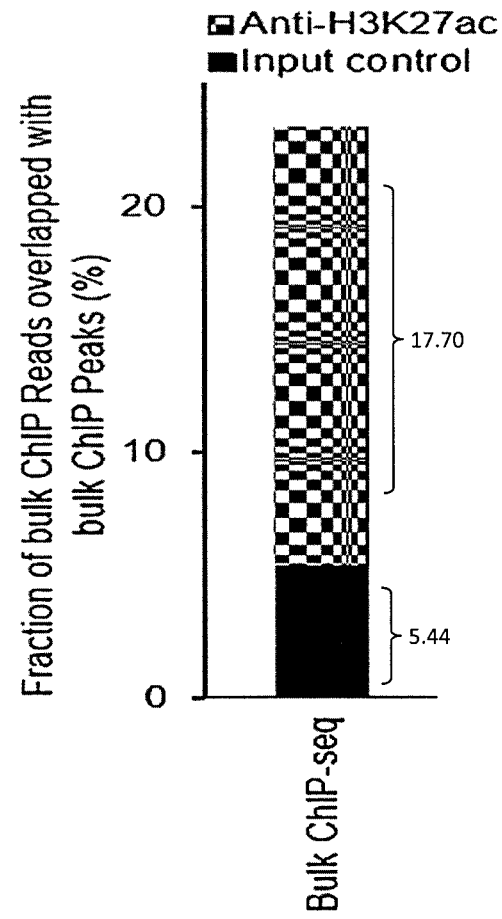
Figure 8D                    Figure 8E

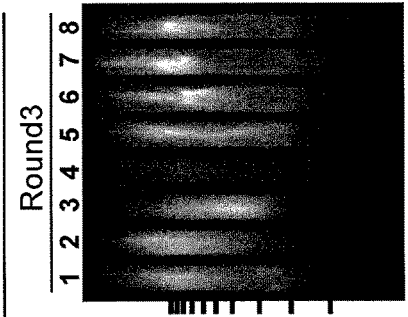
Figure 9C
Figure 9B
Figure 9A
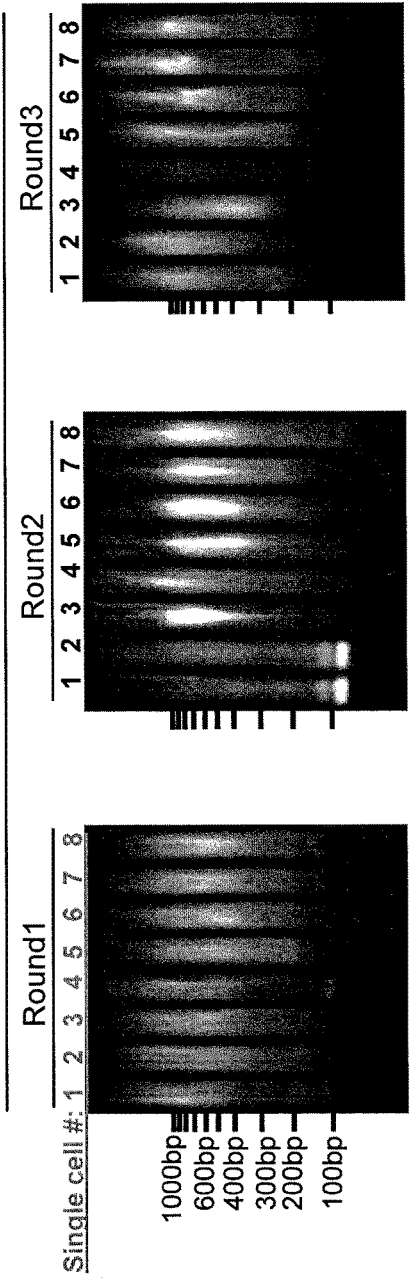
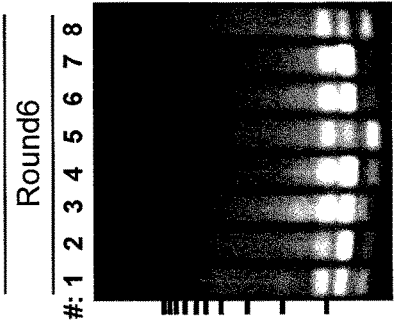
Figure 9F
Figure 9E
Figure 9D
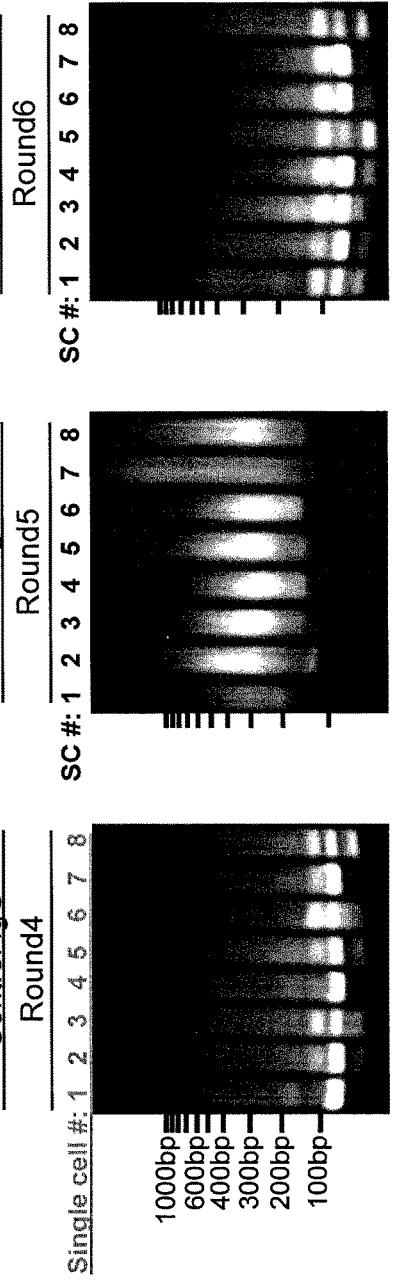

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: synthetic

<400> SEQUENCE: 1

Asn Asn Asn Asn Asn Asn Asn Asn
1               5

METHODS OF PREPARING A RE-USABLE SINGLE CELL AND METHODS FOR ANALYZING THE EPIGENOME, TRANSCRIPTOME, AND GENOME OF A SINGLE CELL

CROSS-REFERENCE TO RELATED APPLICATIONS

This patent application is the U.S. National Phase of International Patent Application No. PCT/US2018/031201, filed May 4, 2018, which claims the benefit of U.S. Provisional Patent Application No. 62/502,247, filed on May 5, 2017, each of which is incorporated by reference in its entirety herein.

STATEMENT REGARDING FEDERALLY SPONSORED RESEARCH OR DEVELOPMENT

This invention was made with Government support under contract number ZIA SC 010355, awarded by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 652 Byte ASCII (Text) file named "744848_ST25.TXT," created on Oct. 31, 2019.

BACKGROUND OF THE INVENTION

The ability to study DNA, RNA, and DNA-bound proteins simultaneously, and determine the location of proteins with and without modifications in the genome of individual cells may be technically challenging. Moreover, many single cells cannot be re-used after the cellular components of the single cell have been studied. The inability to repeat experiments on the same single cell may prevent the application of statistical analysis to the study of the single cell. In addition, some methods of amplifying and sequencing a cell genome may have high error rates and may introduce mutations during the amplification process.

Thus, methods for anchoring the cellular components and creating a re-usable single cell are needed. Methods for analyzing multiple histone modifications, DNA modifications, and DNA binding proteins of individual single cells are needed. Methods for determining the location of an antibody bound to a genome and identifying single cells are needed.

BRIEF SUMMARY OF THE INVENTION

In an embodiment, the invention provides a method for preparing a re-usable single cell by anchoring the cellular components inside the single cell. In some embodiments, the method for preparing a re-usable single cell comprises a nano-scale scaffold to anchor the cellular components inside the single cell. In some embodiments, the nano-scale scaffold is a polyacrylamide nano-scale scaffold. In some embodiments the polyacrylamide nano-scale scaffold is prepared by a method comprising dispersing cells in a solution comprising acrylamide and para-formaldehyde (PFA) to produce dispersed cells; suspending the dispersed cells in acrylamide-N,N'-bis(acryloyl)cystamine or acrylamide-bisacrylamide to produce a cell suspension; and incubating the cell suspension in N,N,N',N'-tetramethylethylenediamine (TEMED) to form a polyacrylamide nano-scale scaffold to anchor the cellular components and create a re-usable single cell.

In some embodiments, the polyacrylamide nano-scale scaffold is prepared by a method comprising isolating single cells or clusters of cells from a tissue section using laser microdissection, or from tissue fragments using various cell-picking systems; suspending the collected cells or clusters of cells in a solution comprising acrylamide-bisacrylamide or acrylamide-N,N'-bis(acryloyl)cystamine to produce a cell suspension; and incubating the cell suspension in the presence of N,N,N',N'-tetramethylethylenediamine (TEMED) to polymerize the acrylamide; to form a polyacrylamide nano-scale scaffold, which anchors the cellular components in a re-usable single cell.

In some embodiments, the single cell is derived by manual isolation from a cell suspension, which cell suspension may be prepared by digestion of a solid tissue.

In some embodiments, the single cell is obtained by a method for automated or semi-automated sorting based on antibody selection or other chemical/biochemical cell characteristics.

In some embodiments, the single cell is obtained from a tissue by tissue microdissection or similar microscopy aided technique.

In some embodiments, the polyacrylamide nano-scale scaffold is prepared by dispersing the cells in a solution comprising about 1% to about 40% acrylamide and about 2% to about 6% PFA. In some embodiments, the dispersed cells are placed in ice for at least about 15 minutes. In some embodiments, the dispersed cells are suspended in a solution comprising about 1% to about 6% acrylamide-N,N'-bis(acryloyl)cystamine or about 1% to about 6% acrylamide-bisacrylamide. In some embodiments, the acrylamide-bisacrylamide or acrylamide-N,N'-bis(acryloyl)cystamine solution further comprises Tris and ammonium persulfate. In some embodiments, the cell suspension is incubated in TEMED in mineral oil.

In some embodiments of the invention, the polyacrylamide nano-scale scaffold is degradable by at least one reducing agent. In some embodiments, the at least one reducing agent is dithiothreitol (DTT). In some embodiments, the polyacrylamide nano-scale scaffold has an average mesh size of about 10 nm to about 40 nm.

In an embodiment, the invention provides a method for analyzing at least one of the genome, epigenome, and transcriptome in a single cell. The method comprises preparing a re-usable single cell according to any of the inventive methods described herein and detecting a modification in at least one of the genome, epigenome, and transcriptome in the single cell. In some embodiments, the method for analyzing at least one of the genome, epigenome, and transcriptome in a single cell comprises detecting at least one of a genomic modification, a deoxyribonucleic acid (DNA) modification, a DNA methylome, a DNA hydroxyl methylome, a histone modification, binding of a histone modifier, modification of a DNA binding protein, and binding of a ribonucleic acid (RNA) polymerase. In some embodiments, the method for analyzing at least one of the genome, epigenome, and transcriptome in the single cell comprises using an antibody to detect one or more modifications in at least one of the genome, epigenome, or transcriptome.

In an embodiment, the invention relates to a method for determining the location of an epigenetic modification in a genome of a single cell. The method comprises preparing a re-usable single cell according to any of the inventive methods described herein, binding an antibody to the epigenetic modification on the genome, and sequencing a portion of the genome of the single cell comprising the epigenetic modification, to determine the location of the epigenetic modification on the genome.

In an embodiment, the invention relates to a method for sequencing genomic DNA from a single cell. The method comprises annealing to genomic DNA on the single cell a first oligonucleotide primer, wherein the first oligonucleotide primer comprises, in a 5' to 3' orientation, a random nucleotide sequence or specific primers for targeted regions with a first ligation sequence (R); extending the sequence of the first random nucleotide sequence using a first DNA polymerase; binding at least one tagged antibody to an epigenetic modification; wherein the antibody is tagged with a polynucleotide comprising, in a 5' to 3' orientation, a first polymerase chain reaction (PCR) amplification sequence, an RNA polymerase promoter sequence, a restriction enzyme site sequence, an antibody barcode sequence, and a second ligation sequence (L); joining the second ligation sequence (L) to the first ligation sequence (R) using a ligation adapter and a DNA ligase to create a ligation product; annealing a second oligonucleotide primer to the ligation product, wherein the second oligonucleotide primer comprises, in a 3' to 5' orientation, a second random nucleotide sequence, a cell barcode sequence, a restriction enzyme site sequence, and a second sequence for PCR amplification; amplifying the ligation product with the annealed second oligonucleotide primer using multiple displacement amplification (MDA) to obtain an MDA-amplified DNA; amplifying the MDA-amplified DNA using PCR, in vitro transcription, and reverse transcription to obtain an amplified genomic DNA fragment; and sequencing the amplified genomic DNA fragment. In some embodiments, the PCR is panhandle PCR, prior to in vitro transcription the method further comprises removing non-specific DNA using DNA digestion, in vitro transcription uses T7 RNA polymerase, and after in vitro transcription the method further comprises purifying RNA using phase separation.

In some embodiments, a method for determining the position of an epigenetic modification in a single cell comprises preparing a re-usable single cell according to any of the inventive methods described herein, annealing to genomic DNA inside the single cell a first oligonucleotide primer; wherein the first oligonucleotide primer comprises, in a 5' to 3' orientation, a first random nucleotide sequence and a first ligation sequence (R); extending the sequence of the first random nucleotide sequence using a first DNA polymerase; binding at least one tagged antibody to an epigenetic modification; wherein the antibody is tagged with a polynucleotide comprising, in a 5' to 3' orientation, a first PCR amplification sequence, an RNA polymerase promoter sequence, a restriction enzyme site sequence, an antibody barcode sequence, and a second ligation sequence (L); joining the second ligation sequence (L) to the first ligation sequence (R) using a ligation adapter and a DNA ligase to create a ligation product; annealing a second oligonucleotide primer to the ligation product, wherein the second oligonucleotide primer comprises in a 3' to 5' orientation a second random nucleotide sequence, a cell barcode sequence, a restriction enzyme site sequence, and a second sequence for PCR amplification; amplifying the ligation product with the annealed second oligonucleotide primer using multiple displacement amplification (MDA) to obtain an MDA-amplified DNA; amplifying the MDA-amplified DNA using PCR, in vitro transcription, and reverse transcription to obtain an amplified genomic DNA fragment; and sequencing the amplified genomic DNA fragment.

In some embodiments of the invention, the re-usable single cell is incubated in the presence of at least one antibody to an epigenetic modification and further incubated in the presence of a control antibody. In some embodiments, the epigenetic modification is a histone modification. In some embodiments, the re-usable single cell is incubated simultaneously in the presence of the control antibody and the antibody specific for at least one epigenetic modification. In some embodiments, the position of multiple epigenetic modifications is determined in the same single cell.

In some embodiments, the re-usable single cell is incubated in the presence of at least one antibody selected from anti-5-methylcytosine antibody, anti-5-hydroxymethylcytosine antibody, anti-histone H3K27ac antibody, anti-histone H3K27me3 antibody, anti-histone H3K9ac antibody, anti-histone H3K9me3 antibody, anti-transcription factor antibody, anti-Med1 antibody, anti-HP1 antibody, anti-HDAC1 antibody, anti-P300 antibody, anti-STAT1 antibody, and anti-RNA polymerase II antibody.

In an embodiment, the invention relates to a method for identifying an epigenetic pathway to cancer. The method comprises determining the position of at least one epigenetic modification in one or more re-usable single cells using any of the inventive methods described herein, wherein the patient has a history of one or more of gammopathies, intestinal polyps, cervical dysplasia, and Myelodysplastic Syndromes (MDS), pre-cancerous lesions or conditions, including (but not limited to) cirrhosis, liver steatosis, Crohn's disease, ulcerative colitis, gastritis (atrophic), ductal in situ carcinoma, oral leukoplakia, skin T-cell infiltration syndromes, and bladder carcinoma in situ that developed to cancer.

Still another embodiment of the invention provides a method for identifying an epigenetic pathway to cancer comprising determining the position of at least one epigenetic modification in one or more single cells using any of the inventive methods described herein, wherein the patient has a history of pre-neoplastic lesions that developed to cancer.

In some embodiments, the invention relates to a method for mapping the genetic evolution from pre-neoplastic cells to cancer comprising determining the position of at least one epigenetic modification in one or more single cells using any of the inventive methods described herein, wherein the epigenetic modification identifies the founder cell among pre-neoplastic cells.

Another embodiment of the invention provides a method for identifying a cell of origin of cancer cells based on determining the position of at least one epigenetic modification in one or more single cells using any of the inventive methods described herein.

Another embodiment of the invention provides a method for the identification of cancer stem cells within a tumor.

Another embodiment of the invention provides a method for determining targeted approaches to cancer cell treatment related to rare driver mutations and epigenetic alterations.

Another embodiment of the invention provides a method for recognizing and predicting the emergence of treatment resistance in cancer.

Another embodiment of the invention provides a method for directing treatment when resistance to treatment has emerged.

In some embodiments, the invention provides a high throughput method for sequencing genomic DNA comprising at least one epigenetic modification.

In an embodiment, the invention provides a kit for preparing a re-usable single cell. In some embodiments, the kit comprises formaldehyde and an acrylamide monomer, acrylamide-N,N'-bis(acryloyl)cystamine or acrylamide-bisacrylamide, TEMED in mineral oil, and instructions to create a scaffold to prepare a re-usable single cell. In some embodiments, the kit for creating a re-usable single cell further comprises at least one antibody to at least one epigenetic modification, and instructions for using the at least one antibody to determine the location of the at least one epigenetic modification on the re-usable single cell.

BRIEF DESCRIPTION OF THE SEVERAL VIEWS OF THE DRAWING(S)

Figure 3:
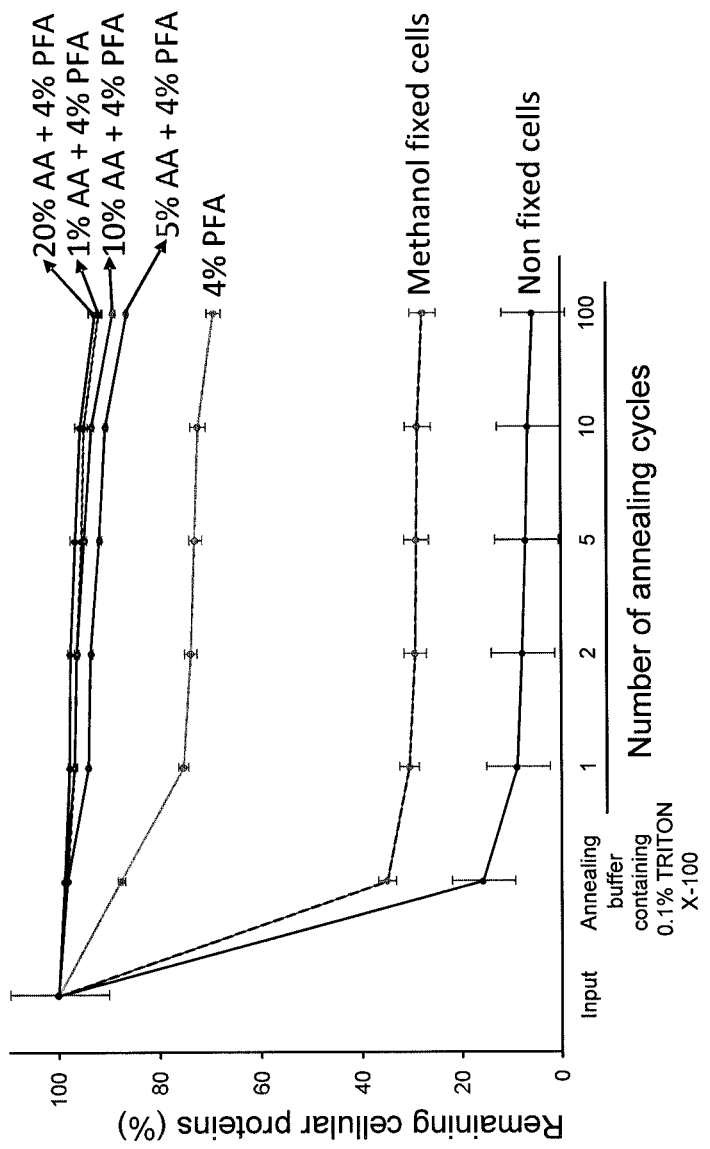

FIG. 3 is a graph showing the percentage of cellular proteins retained in single cells after the cell has undergone different numbers of heating/cooling cycles. The cell was either not fixed, fixed with methanol, fixed with 4% formaldehyde (4% PFA), fixed with 4% PFA and 1% acrylamide (1% AA), fixed with 4% PFA and 5% AA, fixed with 4% PFA and 10% AA, or fixed with 4% PFA and 20% AA.

Figure 4:
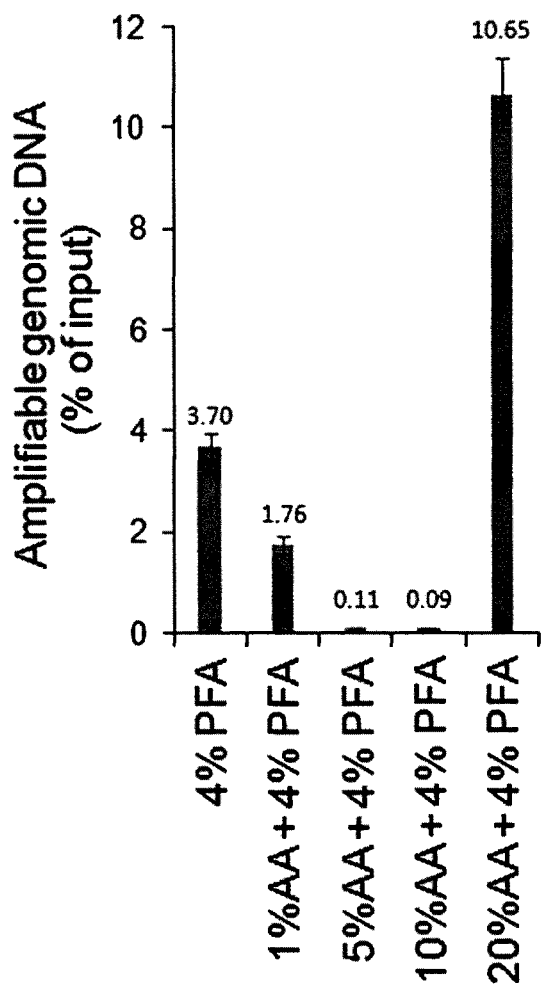

FIG. 4 is a graph showing the percentage of amplifiable genomic DNA retained in single cells after the fixative is removed by treatment with dithiothreitol (DTT). The cell was fixed with either 4% PFA, 4% PFA and 1% AA, 4% PFA and 5% AA, 4% PFA and 10% AA, or 4% PFA and 20% AA.

Figure 5A:
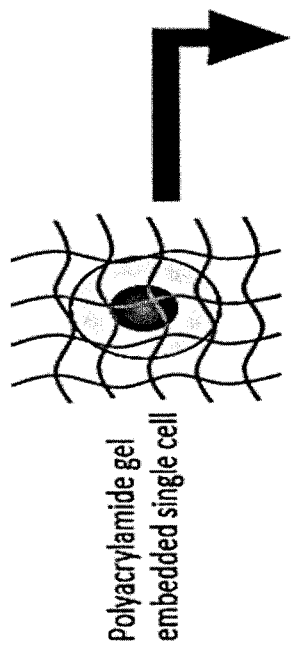
Figure 5A:
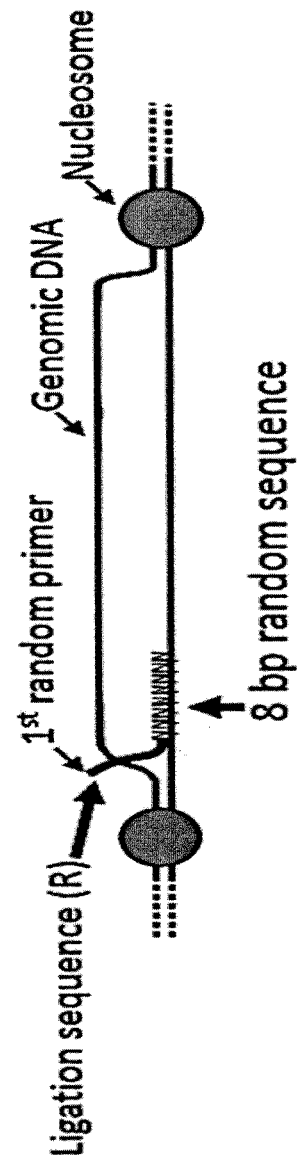

FIG. 5A is a diagram illustrating Step 1 of the method of an embodiment of the invention: anneal first random primer to genomic DNA. The 8 bp random sequence of NNNNNNNN is SEQ ID NO: 1.

Figure 5B:
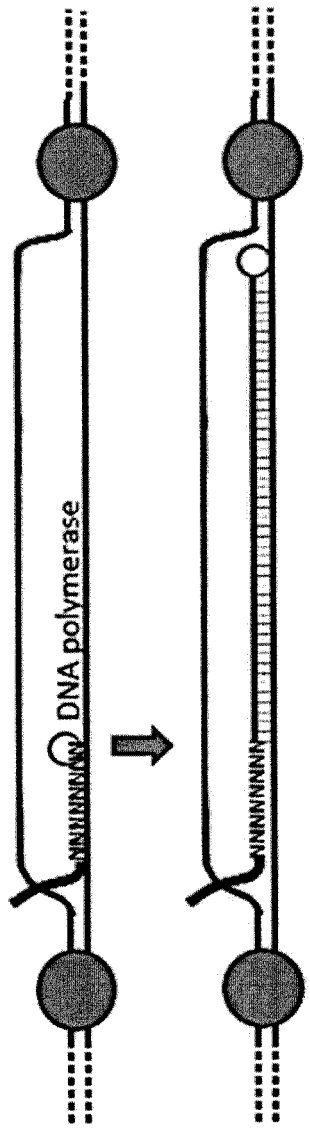

FIG. 5B is a diagram illustrating Step 2 of the method of an embodiment of the invention: extension of the first random primer to stabilize the binding and acquire locational information. NNNNNNNN is SEQ ID NO: 1.

Figure 5C:
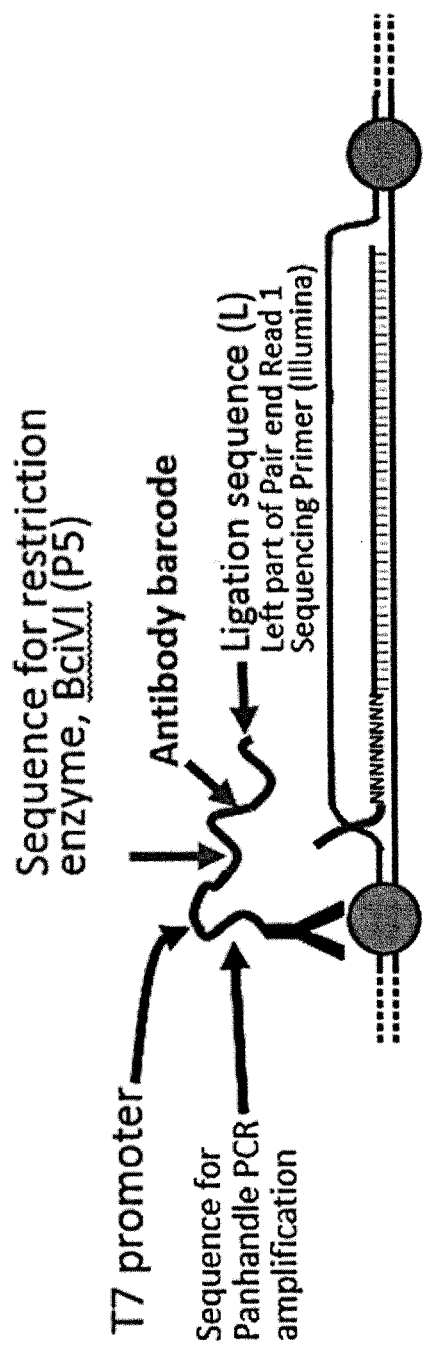

FIG. 5C is a diagram illustrating step 3 of the method of an embodiment of the invention: antibody (Ab) binding to a target. NNNNNNNN is SEQ ID NO: 1.

Figure 5D:
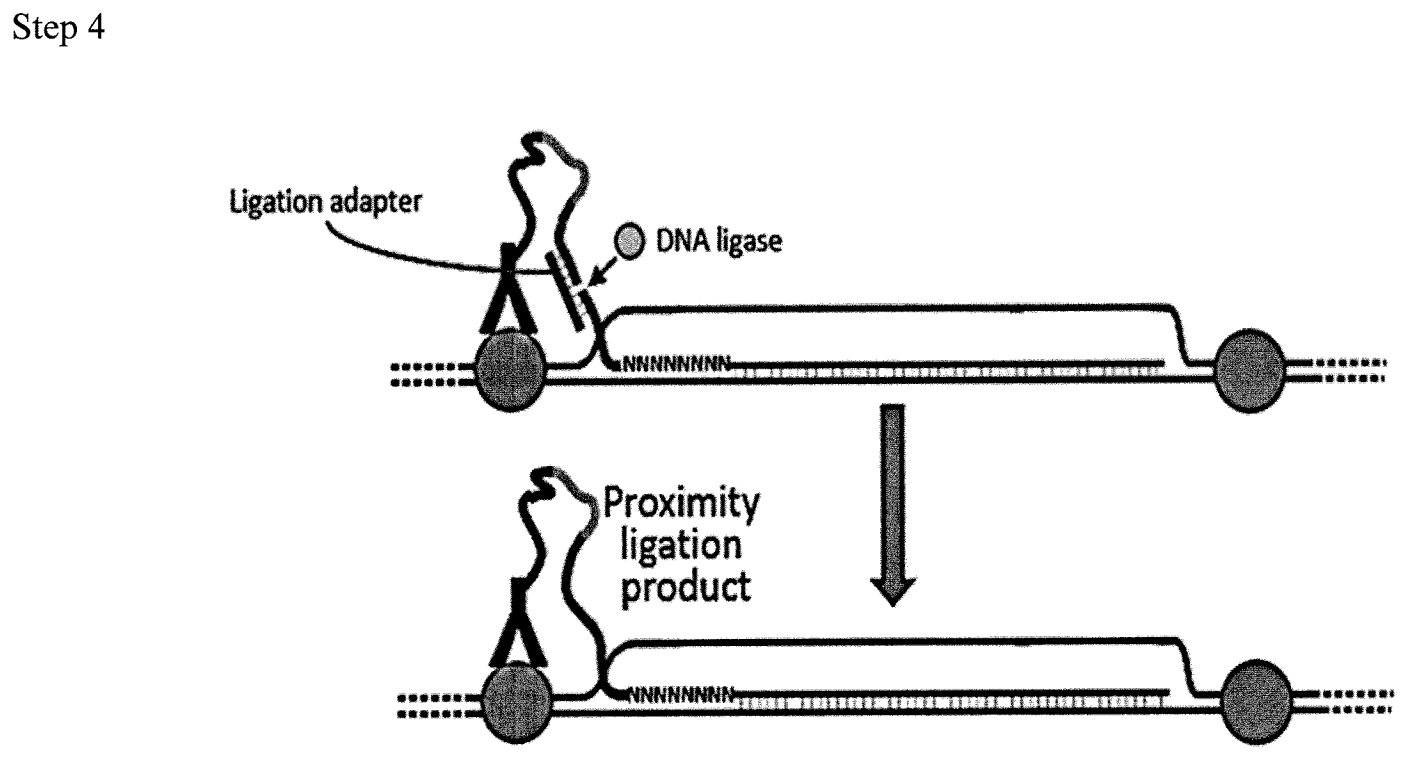

FIG. 5D is an illustration of step 4 of the method of an embodiment of the invention: proximity ligation of Ab probe and first random primer with a ligation adapter. NNNNNNNN is SEQ ID NO: 1.

Figure 5E:
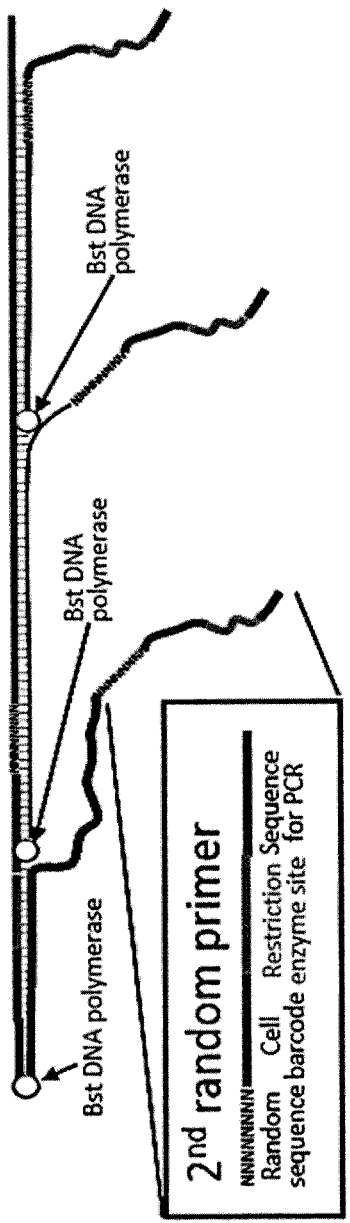
Figure 5E:
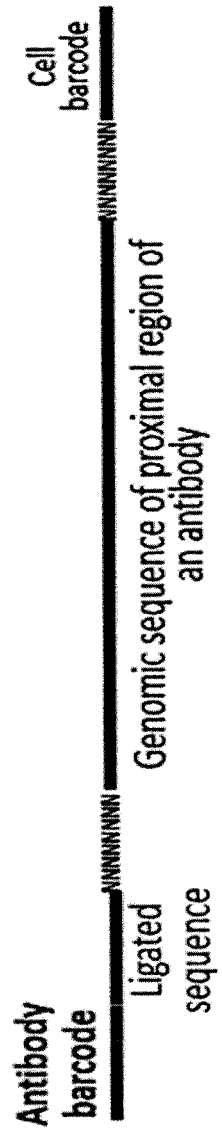

FIG. 5E is an illustration of steps 5 and 6 of the method of an embodiment of the invention. Step 5 is multiple displacement amplification (MDA) using a second random primer. NNNNNNNN is SEQ ID NO: 1. Step 6 is amplification by Panhandle PCR, in vitro transcription and reverse transcription.

Figure 5F:
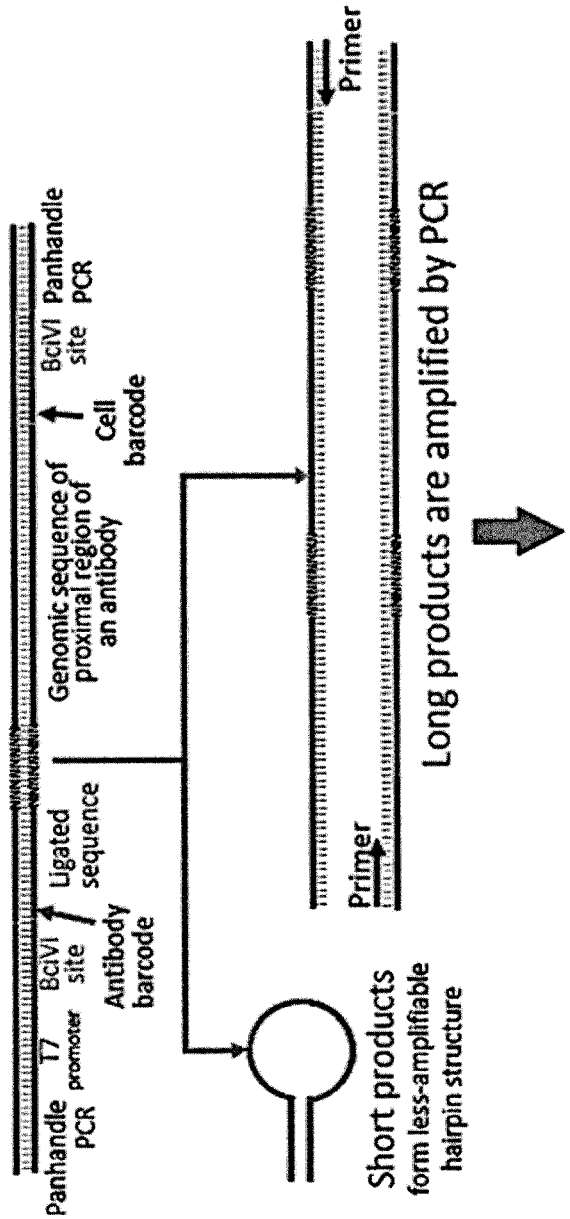

FIG. 5F is an illustration of further details of step 6 of the invention: the removal of non-specific products and amplification of specific products by Panhandle PCR (to enrich longer products and reduce short products in IVT) (step 6-1).

Figure 5G:
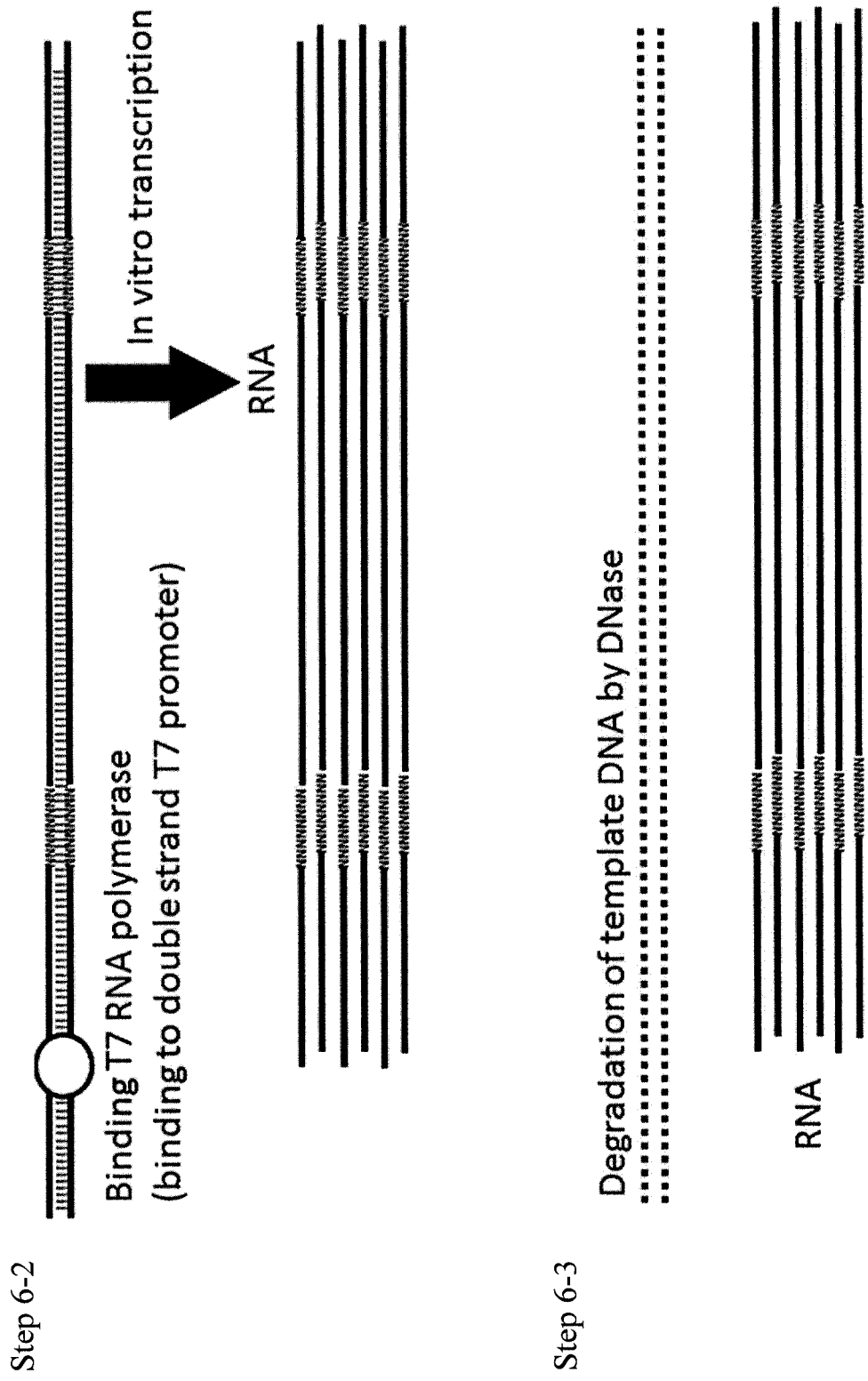

FIG. 5G is an illustration of in vitro transcription (step 6-2, top) and DNAse treatment and RNA purification (step 6-3, bottom). NNNNNNNN is SEQ ID NO: 1.

Figure 5H:
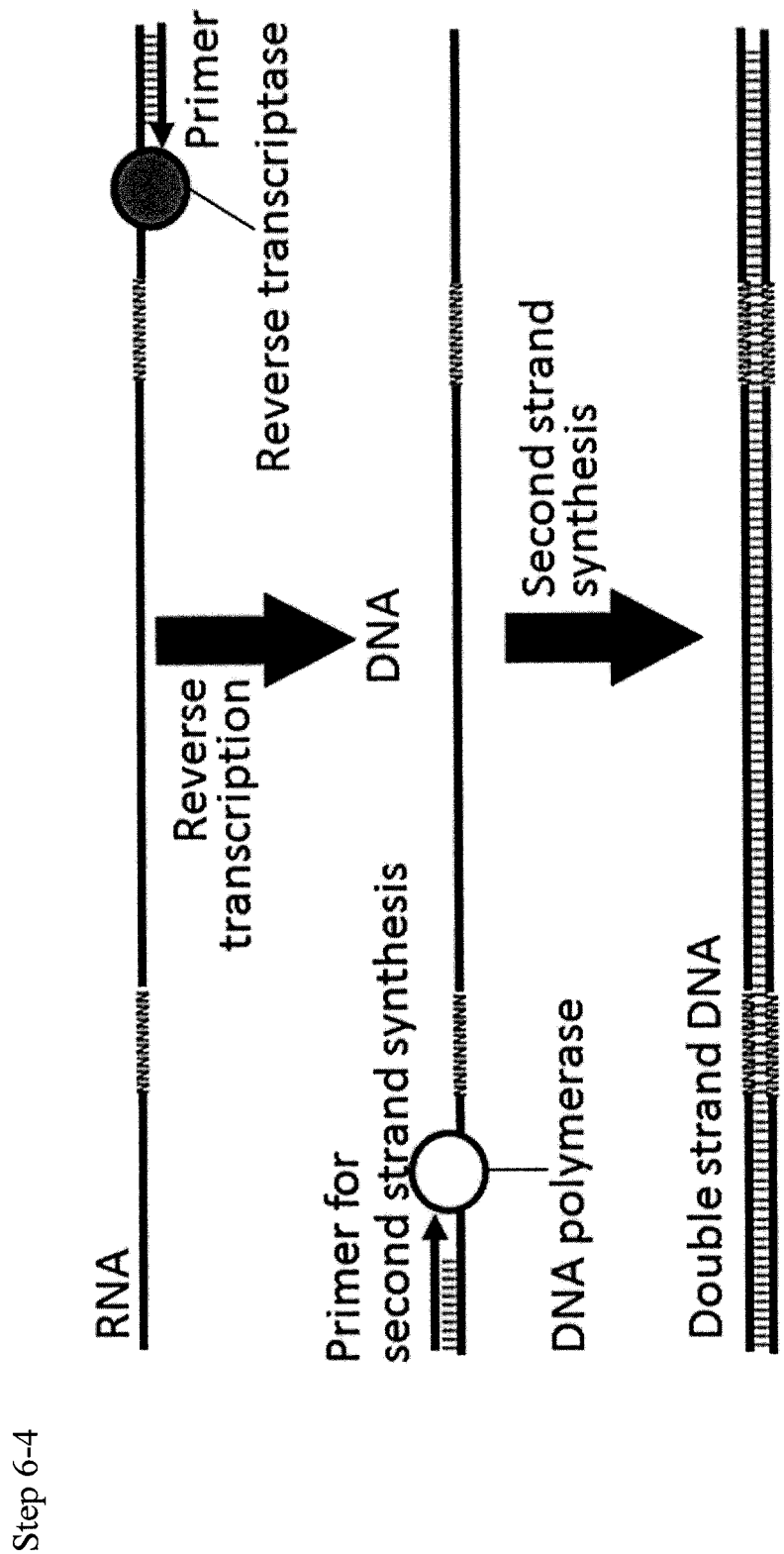

FIG. 5H is an illustration of reverse transcription according to an embodiment of the invention (step 6-4). NNNNNNNN is SEQ ID NO: 1.

Figure 5I:
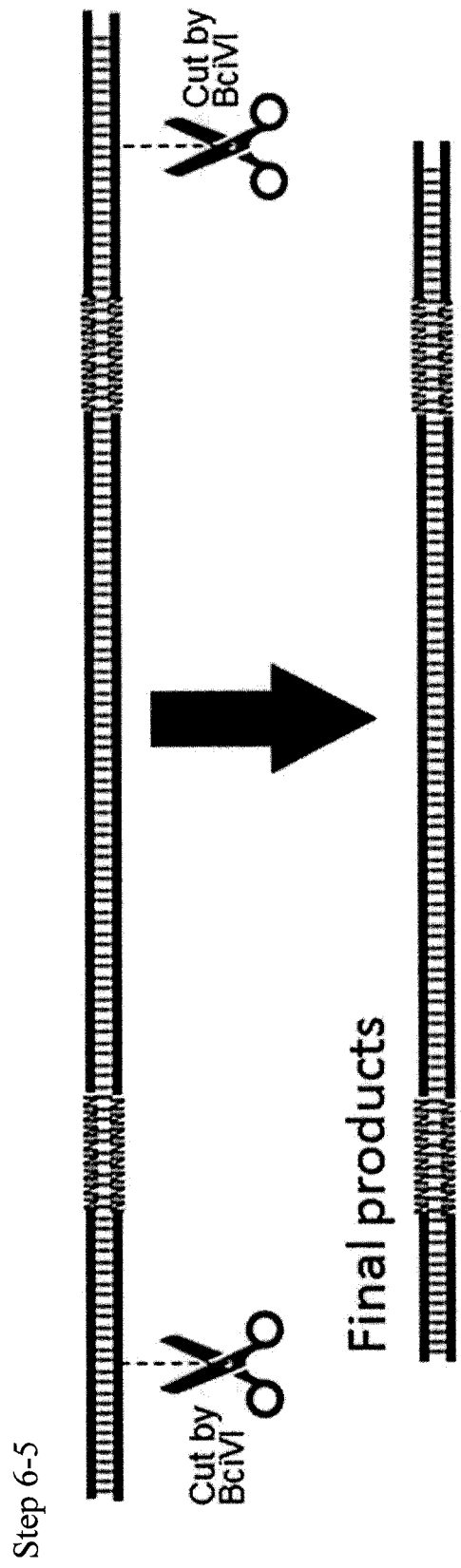

FIG. 5I is an illustration of digestion by the restriction enzyme, BciVI, according to an embodiment of the invention (step 6-5). NNNNNNNN is SEQ ID NO: 1.

Figure 6:
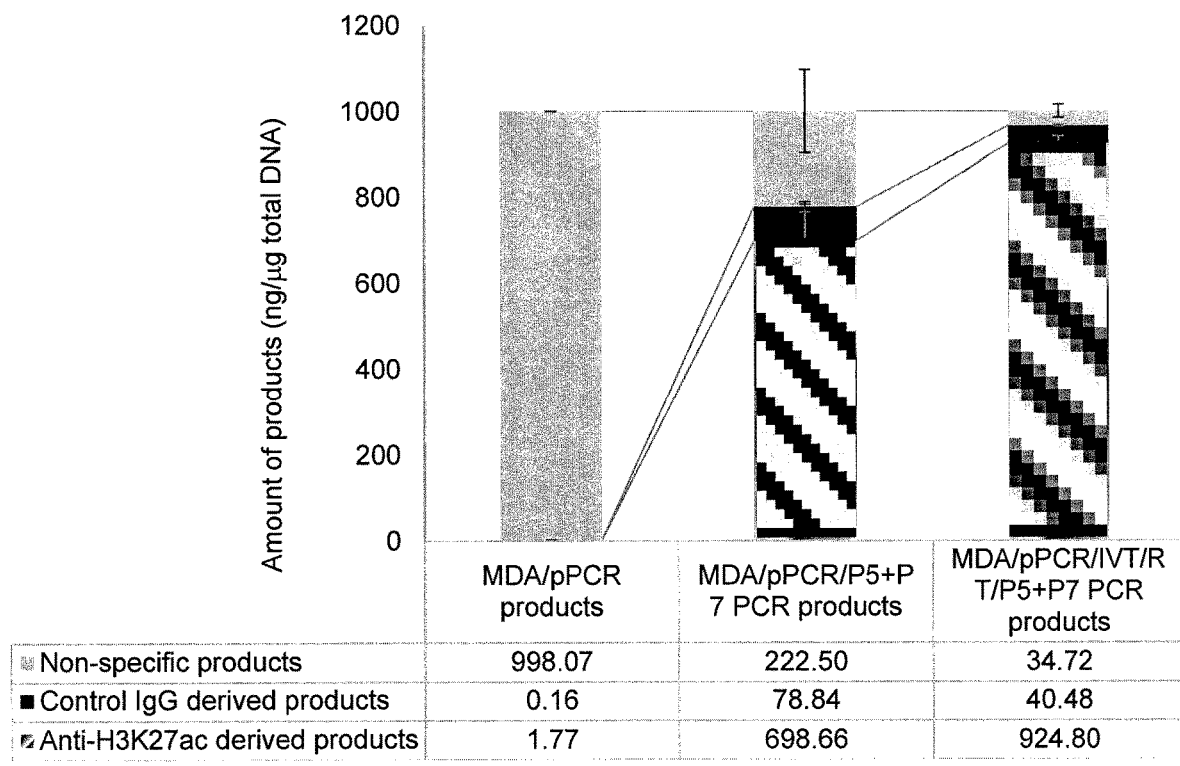

FIG. 6 is a graph showing the amounts of DNA products obtained (non-specific, control antibody-derived, or anti-H3K27ac-antibody derived) using antibody-specific primers, expressed as ng/µg of total DNA.

Figure 7A:
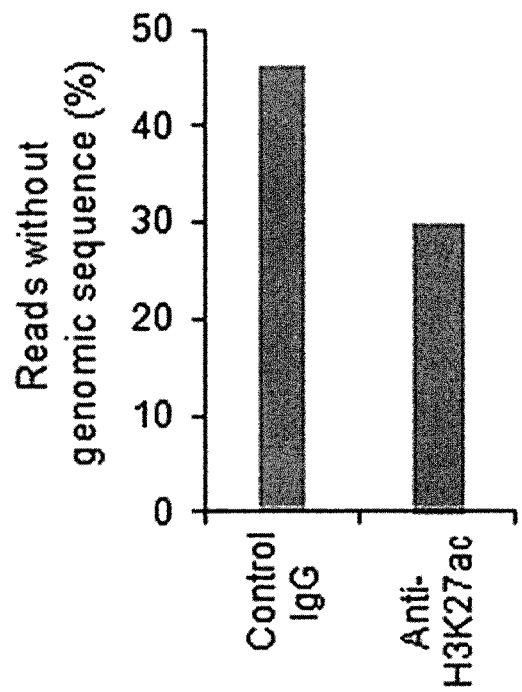

FIG. 7A is a graph of the percentage of DNA products (sequences) without genomic sequence obtained with a control antibody or with anti-H3K27ac antibody.

Figure 7B:
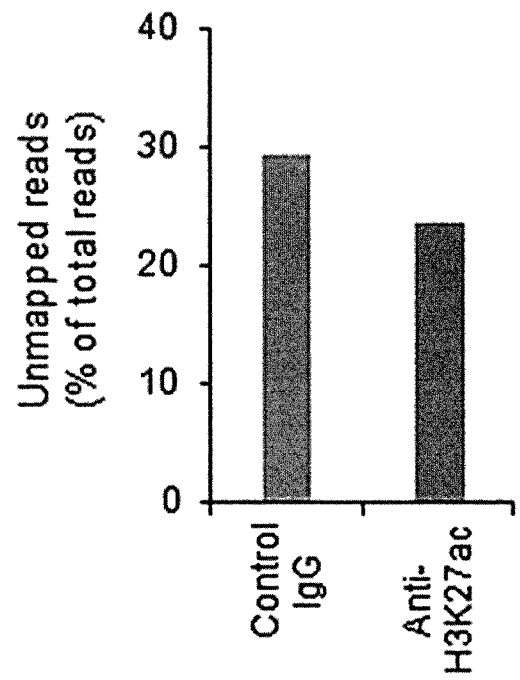

FIG. 7B is a graph of the percentage of total DNA products which are not mapped to the human genome obtained with a control antibody or with anti-H3K27ac antibody.

Figure 8A:
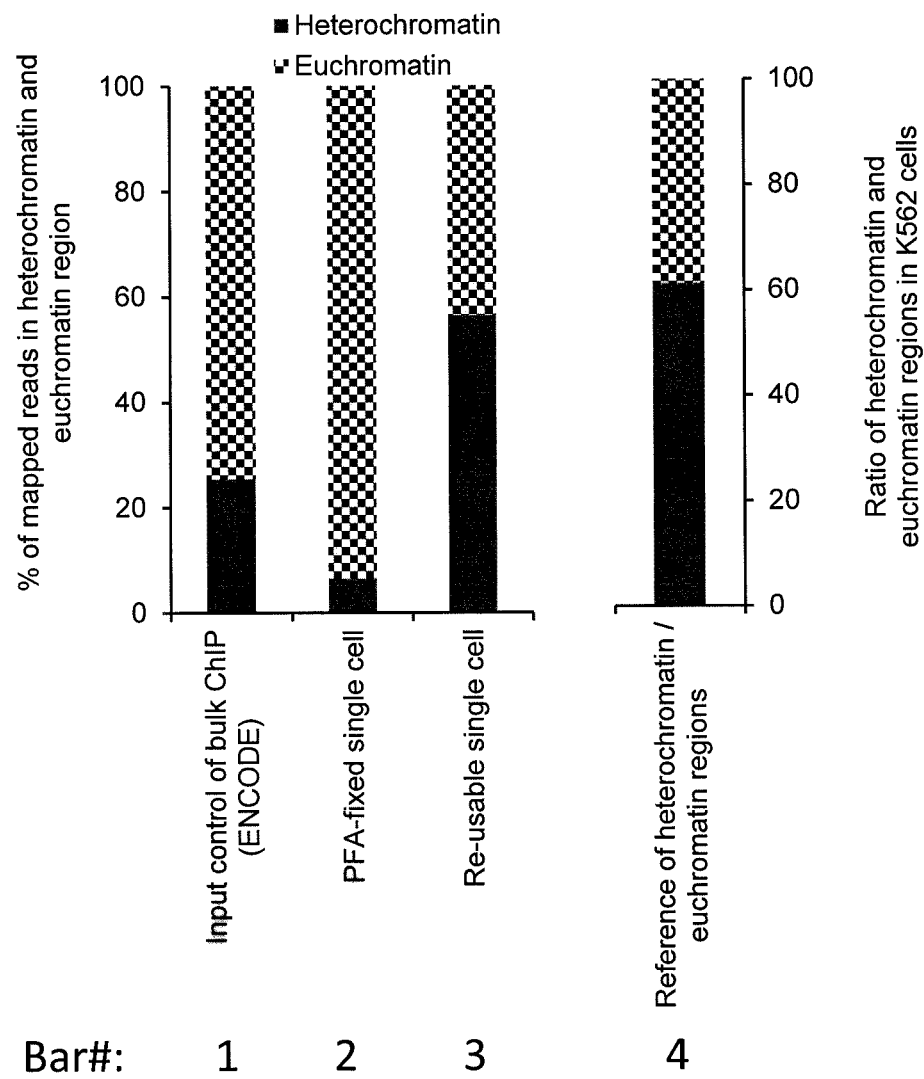

FIG. 8A is a graph of the percentage of mapped reads in heterochromatic and euchromatin regions derived from: input control of bulk ChIP in K562 cells (Bar #1, left); a PFA-fixed single-cell (Bar #2); a re-usable single cell produced according to embodiments of the invention (Bar #3); and reference heterochromatin/euchromatin regions in K562 cells (Bar #4) is identified by automated chromatin-state discovery algorithm, ChromHMM performed by Encyclopedia of DNA Elements (ENCODE).

FIGS. 8B and 8C are graphs showing the overlap of the fraction of single-cell reads and ChIP reads compared to bulk ChIP peaks. The left panel shows the number of single-cell reads overlapped with peaks of bulk ChIP-seq in the "non-fixed single cell" negative control and in a re-usable single cell produced according to embodiments of the invention. The right panel shows the number of reads of bulk ChIP-seq in statistically identified peaks. In the non-fixed single cell, proteins and DNA were not anchored to a polyacrylamide scaffold. In the re-usable single cell, proteins and DNA were anchored to a polyacrylamide scaffold. FIGS. 8D and 8E are graphs showing the overlap of the fraction of single-cell reads and bulk ChIP reads compared to bulk ChIP peaks. The left panel shows a number of single cell reads overlapped with peaks of bulk ChIP-seq in the non-fixed single cell control and re-usable single cell according to embodiments of the invention. The right panel shows a number of reads of bulk ChIP-seq in statistically identified peaks. In the non-fixed single cell, proteins and DNA were not anchored to a polyacrylamide scaffold. In the re-usable single cell, proteins and DNA were anchored to a polyacrylamide scaffold.

FIG. 9A shows reproduced pictures of gels run with products of 8 single cells produced according to embodiments of the invention. FIG. 9A shows production of DNA products and DNA size distribution using antibodies for histone modifications, H3K27ac and H3K27me3 with 8 re-usable single cells (Single cell ID number 1-8) produced according to embodiments of the invention. FIG. 9A is a result of agarose gel electrophoresis loaded with final DNA products of Round1 experiment derived from 8 re-usable single cells produced according to embodiments of the invention. Area (A) of the gels includes products containing a genomic sequence and antibody barcodes. Area (B) of the gels includes byproducts.

FIG. 9B shows reproduced pictures of gels run with products of the same 8 single cells used in FIG. 9A produced according to embodiments of the invention. FIG. 9B shows production of DNA products and DNA size distribution using antibodies for histone modifications, H3K27ac and H3K27me3 with the 8 re-usable single cells, which are used in experiments of FIG. 9A. FIG. 9B is a result of agarose gel electrophoresis loaded with final DNA products of Round2 experiment derived from the 8 re-usable single cells produced according to embodiments of the invention. Area (A) of the gels includes products containing a genomic sequence and antibody barcodes. Area (B) of the gels includes byproducts. FIGS. 9A and 9B support reusability of the re-usable single cells produced according to embodiments of the invention.

FIG. 9C shows reproduced pictures of gels run with products of the same 8 single cells used in FIGS. 9A and 9B produced according to embodiments of the invention. FIG. 9C shows production of DNA products and the DNA size distribution using antibodies for histone modifications, H3K27ac and H3K27me3 with the 8 re-usable single cells, which are used in experiments of FIGS. 9A and 9B. FIG. 9C is a result of agarose gel electrophoresis loaded with final DNA products of Round3 experiment derived from the 8 re-usable single cells produced according to embodiments of the invention. Area (A) of the gels includes products containing a genomic sequence and antibody barcodes. Area (B) of the gels includes byproducts. FIGS. 9A, 9B, and 9C support reusability of the re-usable single cells produced according to embodiments of the invention.

FIG. 9D shows production of DNA products using the antibodies for DNA associated proteins, heterochromatin protein 1 (HP1) and mediator complex subunit 1 (Med1) with the 8 single cells produced according to embodiments of the invention. Area (A) of the gels includes products containing a genomic sequence and antibody barcodes. Area (B) of the gels includes byproducts. FIGS. 9A, 9B, 9C and 9D indicate re-usability of the 8 single cells, and feasibility of multiplexed analysis for different types of epigenetic markers and regulators, histone H3K27ac, histone H3K27me3, HP1 and Med1 in the same single cells.

FIG. 9E shows production of DNA products using the antibodies for DNA modifications, methyl cytosine and hydroxymethyl cytosine with the 8 single cells produced according to embodiments of the invention. Area (A) of the gels includes products containing a genomic sequence and antibody barcodes. Area (B) of the gels includes byproducts. FIGS. 9A, 9B, 9C, 9D, and 9E indicate re-usability of the 8 single cells, and feasibility of multiplexed analysis for different types of epigenetic makers and regulators, histone H3K27ac, histone H3K27me3, HP1, Med1, DNA methylation, and DNA hydroxy methylation in the same single cells.

FIG. 9F shows production of DNA products using the antibodies for RNA polymerase II with the 8 single cells produced according to embodiments of the invention. Area (A) of the gels includes products containing a genomic sequence and antibody barcodes. Area (B) of the gels includes byproducts. FIGS. 9A, 9B, 9C, 9D, 9E, and 9F indicate re-usability of the 8 single cells, and feasibility of multiplexed analysis for RNA transcriptome and epigenetic markers in the same single cells.

Figure 9G:
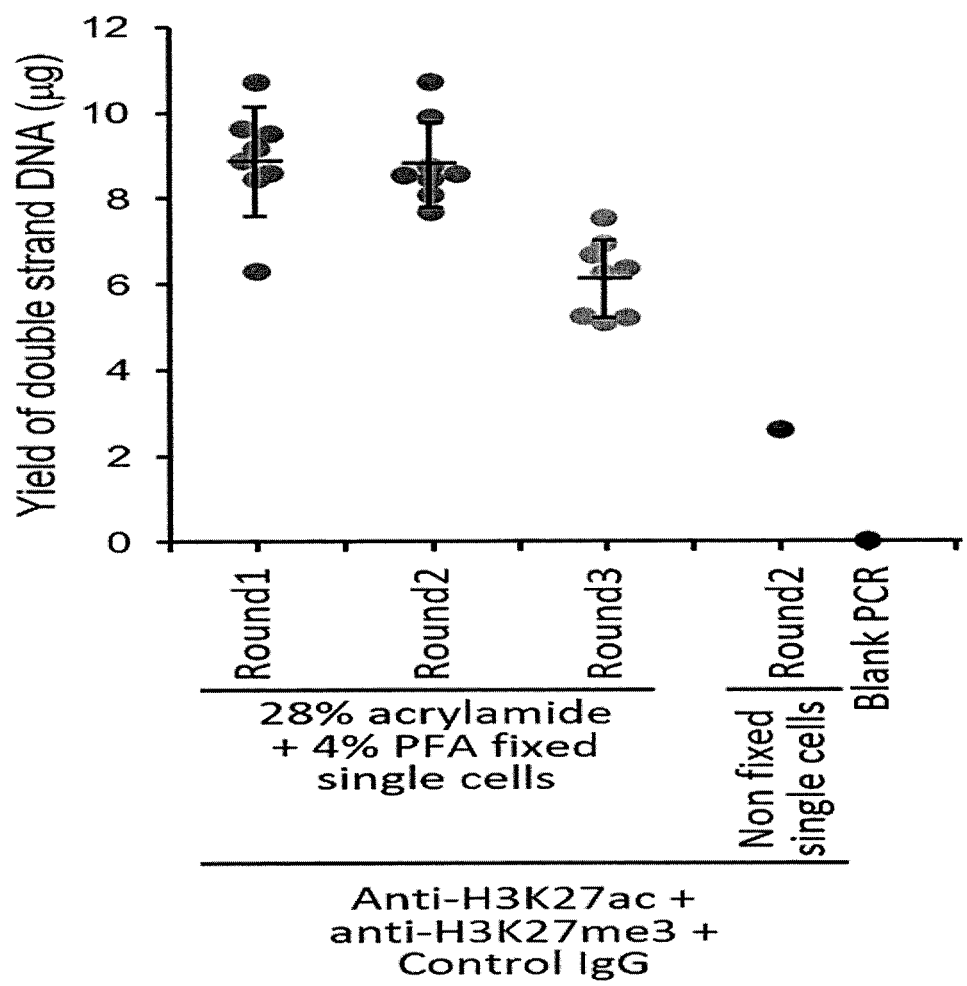

FIG. 9G is a graph of the yield of double-stranded DNA of final products containing genomic sequence and antibody barcodes derived from the single cells of Round 1, Round 2 and Round 3 of 9A, 9B, and 9C, respectively.

Figure 10:
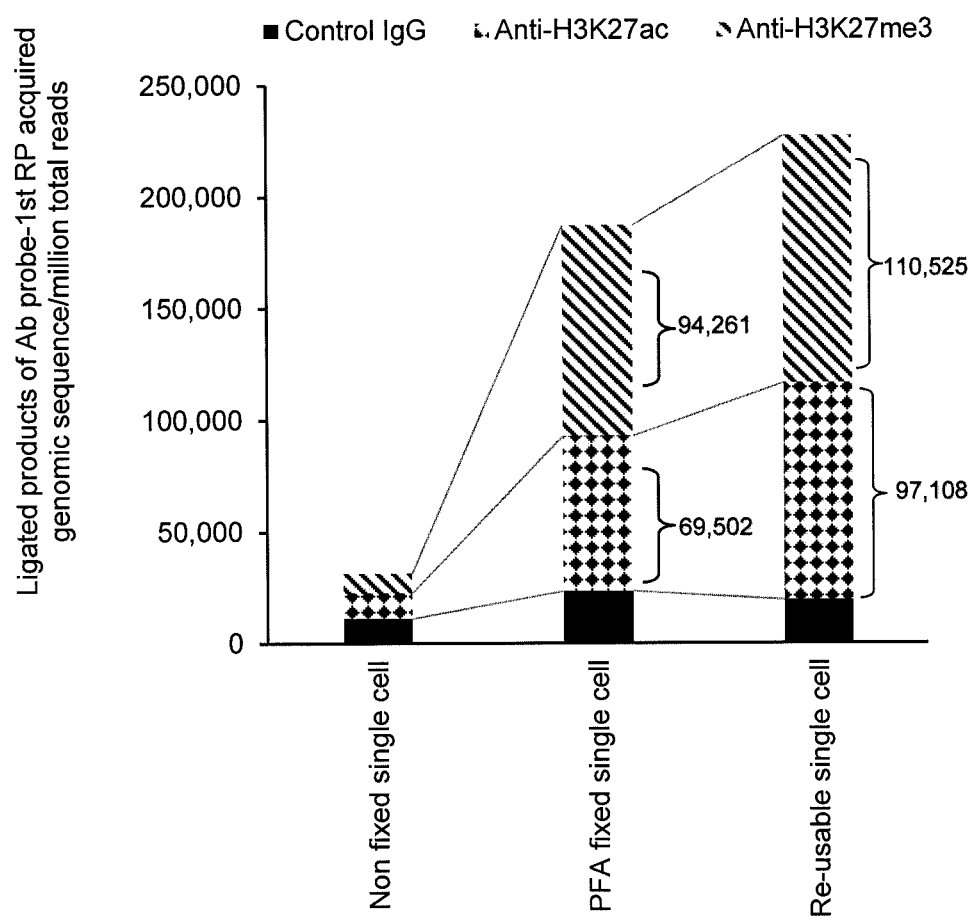

FIG. 10 is a bar graph showing the numbers of reads containing the DNA barcode of anti-H3K27me3 antibody (striped portion); the number of reads containing the DNA barcode of anti-H3K27ac antibody (diamond portion); and the number of reads containing the DNA barcode of control IgG (black portion) in the non-fixed single cell, PFA-fixed single cell, and re-usable single cell produced according to embodiments of the invention.

DETAILED DESCRIPTION OF THE INVENTION

The ability to define the genetic composition of individually isolated cells can be technically challenging. Cells are controlled by three types of inheritable codes. The first code is defined by the DNA sequence, also referred to as the genome. The second code is defined by DNA modifications, such as DNA methylation, DNA hydroxymethylation and other DNA modifications. The third code is defined by histone modifications, which control the accessibility of the cell transcriptional machinery to the genome. The first code is translated by the cell transcriptional machinery, which is controlled by the second and third codes. Errors in each or all these codes may be the cause of many diseases in humans. Therefore, it would be advantageous to decode all of these three codes in individual cells to define the genetic composition of a cell, and eventually correct genetic errors. These errors can occur from an insult to cells, or can occur accidentally, randomly and stochastically. Currently, there are three issues that prevent decoding these three codes in the same single cell. The first issue is an inability to repeat experiments on the same single cell. This may prevent the acquisition of reliable data from each single cell. The second issue is an inability to analyze multiple histone modifications in the same single cells. This may prevent decoding "histone codes" comprising multiple histone modifications. The third issue is an inability to decode the three codes, and transcriptional output from the combined effect of the three codes in individual single cells. This may prevent more comprehensive signatures of normal and diseased cells. Moreover, many single cells cannot be re-used after the cellular components of the single cell have been studied. The inability to repeat experiments on the same single cell may prevent the application of statistical analysis to the study of the single cell. In addition, some methods of amplifying and sequencing a cell genome may have high error rates and may introduce mutations during the amplification process.

Tumors cells may be induced by a combination of genetic and epigenetic alterations. Thus, the identification of genetic and epigenetic modifications may be useful for cancer research and treatment.

Epigenomics includes the study of epigenetic modifications to the genetic material of a cell, also referred to as the epigenome. Epigenetics includes the study of heritable changes that are distinct from changes in DNA sequence. Epigenetic changes may include, for example, covalent modifications to the DNA bases or histone proteins that make up chromatin. Epigenetic changes can be influenced by the environment and transmitted through DNA replication.

The transcriptome includes the set of all messenger RNA molecules in one cell or a population of cells. It differs from the exome in that it includes only those RNA molecules found in a specified cell population, and usually includes the amount or concentration of each RNA molecule in addition to the molecular identities.

Altered DNA and histone methylation may play a role in the progression of Myelodysplastic syndromes (MDS) and acute myelogenous leukemia (AML). AML is a hematologic malignancy characterized by the clonal expansion of myeloid blasts. MDS identifies a group of bone marrow disorders characterized by the failure of the bone marrow to produce blood cells. It is estimated that about 30% of MDS patients progress to AML within a year from diagnosis. It is believed that epigenetic modifications may play a role in the development of AML from MDS.

In an embodiment, the invention relates to methods for preparing a re-usable single cell by anchoring the cellular components inside the single cell. In some embodiments, a nano-scale scaffold anchors the cellular components inside the single cell. In some embodiments, the nano-scale scaffold is a polyacrylamide nano-scale scaffold. Cellular components may include any of a variety of substances of which cells are composed, such as membranes, organelles, proteins, deoxyribonucleic acid (DNA), and ribonucleic acid (RNA). The polyacrylamide nano-scale scaffold may anchor cellular components such as, for example, proteins inside the single cell even after repeated experiments. The polyacrylamide nano-scale scaffold may anchor DNA in a single cell, and the DNA may be used for further study even after removing the nano-scale scaffold using a reducing agent such as dithiothreitol (DTT).

In an embodiment, the polyacrylamide nano-scale scaffold is prepared by dispersing cells or nuclei in a solution comprising acrylamide and paraformaldehyde (PFA) to produce dispersed cells; suspending the dispersed cells in a solution comprising acrylamide-N,N'-bis(acryloyl)cystamine or acrylamide-bisacrylamide to produce a cell suspension; and incubating the cell suspension in the presence of N, N, N',N'-tetramethyl ethylene diamine (TEMED) to polymerize the acrylamide to form a polyacrylamide nano-scale scaffold which anchors the single cell cellular components in a re-usable single cell.

In another embodiment, the polyacrylamide nano-scale scaffold is prepared by isolating single cells or clusters of cells from a tissue section using laser microdissection, or from tissue fragments obtained using various cell-picking systems; suspending the collected cells or clusters of cells in a solution comprising acrylamide-bisacrylamide or acrylamide-N,N-bis(acryloyl)cystamine to produce a cell suspension; and incubating the cell suspension in the presence of N,N,N',N'-tetramethylethylenediamine (TEMED) to polymerize the acrylamide; to form a polyacrylamide nano-scale scaffold, which anchors the cellular components in a re-usable single cell.

In some embodiments, the cells are incubated in the presence of TEMED for at least about 30 minutes to at least about 2 hours. In some embodiments, the cells are incubated in the presence of TEMED for at least about 1 hour. In some embodiments the cells are dispersed in a solution comprising about 1% to about 40% acrylamide and about 2% to about 6% PFA. In some embodiments, the cells are dispersed in a solution comprising about 5% acrylamide to about 30% acrylamide. In some embodiments, the cells are dispersed in a solution comprising about 10% acrylamide to about 40% acrylamide. In some embodiments, the cells are dispersed in a solution comprising about 20% acrylamide to about 30% acrylamide. In some embodiments, the cells are dispersed in a solution comprising about 10% acrylamide to about 20% acrylamide. In some embodiments, the cells are dispersed in a solution comprising about 20% acrylamide. In some embodiments, the cells are dispersed in a solution comprising about 28% acrylamide. In some embodiments, the cells are dispersed in a solution comprising about 10% to about 30% acrylamide. In some embodiments, the cells are dispersed in a solution comprising about 3% PFA to about 5% PFA. In some embodiments, the cells are dispersed in a solution comprising about 4% PFA. As used herein, the term "about," unless otherwise indicated, refers to a value that is no more than about 10% above or below the value being modified by the term.

In some embodiments, the polyacrylamide nano-scale scaffold is prepared by placing the dispersed cells on ice for at least about 15 minutes. In some embodiments, the dispersed cells are placed on ice for at least about 20 minutes. In some embodiments, the dispersed cells are placed on ice for at least about 30 minutes. In some embodiments, the dispersed cells are placed on ice for at least about 45 minutes. In some embodiments, the dispersed cells are placed on ice for at least about 1 hour. In some embodiments, the dispersed cells are placed on ice for at least about 1.5 hours. In some embodiments, after holding on ice, the dispersed cells are washed with Tris buffered saline (TBS) solution.

In some embodiments, the cells are sorted into droplets of a solution comprising acrylamide-bisacrylamide or acrylamide-N,N'-bis(acryloyl)cystamine encapsulated with oil using microfluidic systems, wherein the droplets are polymerized by adding a polymerization initiator.

In some embodiments, TBS is removed, and the cells are resuspended in a solution comprising about 1% to about 6% acrylamide-N,N'-bis(acryloyl)cystamine or about 1% to about 6% acrylamide-bisacrylamide. In some embodiments, the cells are resuspended in a solution comprising about 2% to about 5% acrylamide-N,N'-bis(acryloyl)cystamine or about 2% to about 5% acrylamide-bisacrylamide. In some embodiments, the cells are resuspended in a solution comprising about 2% to about 6% acrylamide-N,N'-bis(acryloyl) cystamine or about 2% to about 6% acrylamide-bisacrylamide. In some embodiments, the cells are resuspended in a solution comprising about 3% to about 4% acrylamide-N,N'-bis(acryloyl)cystamine or about 3% to about 4% acrylamide-bisacrylamide. In some embodiments, the solution comprising acrylamide-bisacrylamide or acrylamide-N,N'-bis(acryloyl)cystamine further comprises Tris and ammonium persulfate.

In some embodiments, the TEMED used to polymerize the acrylamide to form a polyacrylamide nano-scale scaffold is in mineral oil. The amount of oil used may cover the surface of a droplet comprising a single cell. In some embodiments, the amount of oil used is about 10 μl to about 100 μl. In some embodiments, 50 μl of oil containing TEMED are used when polymerizing the acrylamide to form a polyacrylamide nano-scale scaffold. In some embodiments, the polyacrylamide nano-scale scaffold is degradable by at least one reducing agent. To improve whole genome amplification, it may be useful to recover the genomic DNA from the polyacrylamide scaffold by degrading the polyacrylamide scaffold. Thus, in an embodiment of the invention, polyacrylamide gels prepared with 4% acrylamide-bisacrylamide may be useful for single cell epigenome and transcriptome analyses. In some embodiments, the at least one reducing agent is selected from the group consisting of dithiothreitol (DTT), 2-Mercaptoethanol, 3-Mercapto-1,2-propanol, 2-Mercaptoethylamine, and Tris (2-carboxyethyl) phosphine Hydrochloride (TCEP-HCL). The reducing agent may be any reducing agent which may cleave a disulfide bond. Once the disulfide bond is cleaved, the exposed cysteine may be blocked by using alkylating reagents or oxidizing reagents. The alkylating reagents that may be used may be selected from the group consisting of Iodoacetamide, Iodoacidic acid, and N-Ethylmaleimide. The oxidizing reagents that may be used may be selected from the group consisting of 5,5'-Dithiobis(2-nitrobenzoic Acid), 2,2'-Dipyridyl Disulfide, 2,6-Dichloroindophenol, and oxidized form of Glutathione. Other reducing agents that may be used to reduce the nano-scale scaffold are EDTA, Ascorbic acid, and Acidic acid. The nano-scale scaffold may be degraded using 100 nM DTT in ultrapure water for at least about 10 minutes to at least about 1 hour. Being able to degrade the scaffold may allow for recovery of genomic DNA after using the cell for epigenetic analysis.

The polyacrylamide nano-scale scaffold may have any suitable mesh size. In an embodiment of the invention, the polyacrylamide nano-scale scaffold has an average mesh size of about 10 nm to about 40 nm. In some embodiments, the polyacrylamide nano-scale scaffold has an average mesh size of about 15 nm to about 35 nm. In specific embodiments, the polyacrylamide nano-scale scaffold has an average mesh size of about 33 nm.

Any number of cells may be used for preparing a re-usable single cell having the cellular components anchored with a nano-scale scaffold. In some embodiments, $1\times10^6$ cells are dispersed in acrylamide/PFA to prepare a re-usable single cell. The cells used for preparing a re-usable single cell may be any type of cells such as prokaryotic cells (such as bacterial cells or algal cells) or eukaryotic cells (such as insect cells, plant cells, animal cells, protozoan cells, or fungal cells). In some embodiments, the cells used to prepare a re-usable single cell are animal cells. In some embodiments, the cells used to prepare a re-usable single cell are mammalian cells. In specific embodiments, the cells used to prepare a re-usable single cell are K562 cells or MS1 cells. In some embodiments, the method comprises preparing re-usable single cells in bulk.

In an embodiment, the invention relates to a method of using the re-usable single cell to study epigenetic modifications. Antibodies that recognize specific epigenetic modifications may be used to bind to these epigenetic modifications on the genome. In some embodiments in the methods of the invention, a tag, e.g., barcode, may be added to the antibody which recognizes at least one epigenetic modification. This may allow the use of more than one antibody per experiment, permitting the use of control antibodies to determine specificity of the antibody and allowing the analysis of the signal to noise ratio.

In some embodiments, the invention relates to a method for analyzing at least one of the genome, epigenome, or transcriptome in a single cell. The method may comprise preparing a re-usable single cell as described herein with respect to other aspects of the invention, and detecting at least one modification in at least one of the genome, epigenome, or transcriptome in the single cell. In some embodiments of the invention, the method comprises detecting one or more modifications in at least one or two of the genome, epigenome, or transcriptome in the single cell. In an embodiment of the invention, the method comprises detecting one or more modifications in all three of the genome, epigenome, or transcriptome in the single cell. Because the single cell is, advantageously, re-usable, the inventive methods may, advantageously, comprise detecting one or more modifications in two or all three of the genome, epigenome, or transcriptome in the same single cell. The modification in the genome, epigenome, or transcriptome may be any modification in the genome, epigenome, or transcriptome, respectively, as compared to a control genome, epigenome, or transcriptome, respectively. As used herein, the term "genomic modification" may include genome editing, or genome engineering, and may include at least one of the following:

a) Copy number variations,
b) Insertions to the genome,
c) Deletions in the genome,
d) Alterations of genomic sequences,
e) Location of deoxyribonucleic acid (DNA) modifications on the genome,
f) Location of DNA methylation changes on the genome,
g) Location of DNA hydroxy methylation changes on the genome,
h) Location of histone modifications on chromosomes,
i) Location of histone modifiers on chromosomes,
j) Location of DNA bound proteins on chromosomes,
k) Location of RNA polymerases on the genome/chromosomes,
l) Location of ribonucleic acid (RNA) modifications on RNAs, and
m) Bound proteins to RNA.

The control genome, epigenome, or transcriptome may be the genome, epigenome, or transcriptome of a normal, healthy, or wild-type single cell.

The modification in the genome, epigenome, or transcriptome may include any of a variety of modifications in the genome, epigenome, or transcriptome of the single cell. In this regard, the method may comprise acquiring multi-omics data in a single cell. Such modifications may include a modification in any one or more of a genomic sequence, DNA methylome, DNA hydroxy methylome, histone modification, binding of a histone modifier, DNA binding protein, and binding of RNA polymerase as compared to the genomic sequence, DNA methylome, DNA hydroxy methylome, histone modification, binding of a histone modifier, DNA binding protein, and binding of RNA polymerase, respectively, of a control. In a preferred embodiment, the modification is a histone modification. Further examples of modifications may include DNA methylation, histone acetylation, and histone methylation. The modification may be detected by using an antibody specific to the modification of interest. Some antibodies useful for these analyses are anti-5-methylcytosine antibody, anti-5-hydroxymethylcytosine, anti-histone H3K27ac, anti-histone H3K27me3, anti-histone H3K9ac antibody, anti-histone H3K9me3 antibody, anti-transcription factor antibody, anti-Med1 antibody, anti-HP1 antibody, anti-HDAC1 antibody, anti-P300 antibody, anti-STAT1 antibody, anti-RNA polymerase II antibody, or any other antibodies which may be useful in the acquisition of epigenomic and transcriptome data. Additional antibodies which may be useful in embodiments of methods of the invention include the following: anti-5-methylcytosine antibody, anti-5-hydroxymethylcytosine antibody, anti-histone H3K27ac antibody, anti-histone H3K27me3 antibody, anti-histone H3K9ac antibody, anti-histone H3K9me3 antibody, anti-H3K36me3 antibody, anti-H3K4me1 antibody, anti-H3K4me2 antibody, anti-H3K4me3 antibody, anti-H3K79me2 antibody, anti-H3K79me3 antibody, anti-H3K9ac antibody, anti-H3K9me3 antibody, anti-H4K20me1 antibody, anti-transcription factor antibody, anti-Med1 antibody, anti-Med6 antibody, anti-Med14 antibody, anti-Med26 antibody, anti-HP1 antibody, anti-HDAC1 antibody, anti-HDAC6 antibody, anti-P300 antibody, anti-STAT1 antibody, anti-STAT2 antibody, anti-STAT3 antibody, anti-STAT5A antibody, anti-RNA polymerase II antibody, anti-BDP1 antibody, anti-BRF1 antibody, anti-CBX2 antibody, anti-CBX3 antibody, anti-CEBPZ antibody, anti-CTBP2 antibody, anti-GABPA antibody, anti-GATA3 antibody, anti-GTF3C2 antibody, anti-HDAC2 antibody, anti-HMGN1 antibody, anti-IKZF1 antibody, anti-MAZ antibody, anti-MED26 antibody, anti-MEF2C antibody, anti-NCOR1 antibody, anti-NFATC1 antibody, anti-NFE2 antibody, anti-NFYA antibody, anti-PITX1 antibody, anti-SIN3A antibody, anti-SMARCA4 antibody, anti-TAL1 antibody, anti-TCF3 antibody, anti-UBTF antibody, anti-YY1 antibody, anti-ZBTB33 antibody, anti-ZEB1 antibody, anti-ARID3A antibody, anti-ATF1 antibody, anti-ATF2 antibody, anti-ATF3 antibody, anti-BACH1 antibody, anti-BATF antibody, anti-BCL11A antibody, anti-BCL3 antibody, anti-BCLAF1 antibody, anti-BHLHE40 antibody, anti-BRCA1 antibody, anti-BRF2 antibody, anti-BTF3 antibody, anti-CBX8 antibody, anti-CCNT1 antibody, anti-CCNT2 antibody, anti-CDK9 antibody, anti-CEBPB antibody, anti-CEBPD antibody, anti-CELF1 antibody, anti-CHD1 antibody, anti-CHD2 antibody, anti-CHD4 antibody, anti-CHD7 antibody, anti-CREB1 antibody, anti-CREBBP antibody, anti-CTCF antibody, anti-CTCFL antibody, anti-CUX1 antibody, anti-E2F1 antibody, anti-E2F4 antibody, anti-E2F6 antibody, anti-EBF1 antibody, anti-BACH1 antibody, anti-CCNE1 antibody, anti-CDKN1B antibody, anti-E2F1 antibody, anti-ELF1 antibody, anti-ESR1 antibody, anti-FOS antibody, anti-GATA2 antibody, anti-HDAC8 antibody, anti-HMGB1 antibody, anti-ILF2 antibody, anti-JUNB antibody, anti-JUND antibody, anti-MLL5 antibody, anti-NCOR1 antibody, anti-NF90 antibody, anti-NR4A1 antibody, anti-SMARCA1 antibody, anti-SMARCA2 antibody, anti-EGR1 antibody, anti-ELAVL1 antibody, anti-ELF1 antibody, anti-ELK1 antibody, anti-ELK4 antibody, anti-ESR1 antibody, anti-ESRRA antibody, anti-ETS1 antibody, anti-EZH2 antibody, anti-FAM48A antibody, anti-FLI1 antibody, anti-FOS antibody, anti-FOSL1 antibody, anti-FOSL2 antibody, anti-FOXA1 antibody, anti-FOXA2 antibody, anti-FOXM1 antibody, anti-FOXP2 antibody, anti-GATA1 antibody, anti-GATA2 antibody, anti-GRp20 antibody, anti-GTF2B antibody, anti-GTF2F1 antibody, anti-H2AFZ antibody, anti-H3ac antibody, anti-E2F1 antibody, anti-HCFC1 antibody, anti-HMGN3 antibody, anti-HNF4A antibody, anti-HNF4G antibody, anti-HSF1 antibody, anti-IGF2BP1 antibody, anti-IRF1 antibody, anti-IRF3 antibody, anti-IRF4 antibody, anti-IRF9 antibody, anti-JUN antibody, anti-JUND antibody, anti-KAP1 antibody, anti-KAT2A antibody, anti-KAT2B antibody, anti-KDM1A antibody, anti-KDM4A antibody, anti-KDM5A antibody, anti-KDM5B antibody, anti-LEF1 antibody, anti-MAFF antibody, anti-MAFK antibody, anti-MAX antibody, anti-MBD4 antibody, anti-MEF2A antibody, anti-MTA3 antibody, anti-MXI1 antibody, anti-MYB antibody, anti-MYBL2 antibody, anti-MYC antibody, anti-MYOD1 antibody, anti-MYOG antibody, anti-NANOG antibody, anti-NFIC antibody, anti-NFYB antibody, anti-NR2C2 antibody, anti-NR2F2 antibody, anti-NR3C1 antibody, anti-NRF1 antibody, anti-PABPC1 antibody, anti-PAX5 antibody, anti-PBX3 antibody, anti-PHF8 antibody, anti-PML antibody, anti-POLR2A antibody, anti-POLR3G antibody, anti-POU2F2 antibody, anti-POU5F1 antibody, anti-PPARGC1A antibody, anti-PRDM1 antibody, anti-RAD21 antibody, anti-RBBP5 antibody, anti-RCOR1 antibody, anti-RDBP antibody, anti-RELA antibody, anti-REST antibody, anti-RFX5 antibody, anti-RNF2 antibody, anti-RPC155 antibody, anti-RUNX3 antibody, anti-RXRA antibody, anti-SAP30 antibody, anti-SETDB1 antibody, anti-SIN3AK20 antibody, anti-SIRT6 antibody, anti-SIX5 antibody, anti-SLBP antibody, anti-SMARCB1 antibody, anti-SMARCC1 antibody, anti-SMARCC2 antibody, anti-SMC3 antibody, anti-SP1 antibody, anti-SP2 antibody, anti-SP4 antibody, anti-SPI1 antibody, anti-SREBP1 antibody, anti-SREBP2 antibody, anti-SRF antibody, anti-SUPT5H antibody, anti-SUZ12 antibody, anti-T7Tag antibody, anti-TAF1 antibody, anti-TAF7 antibody, anti-TBL1XR1 antibody, anti-TBP antibody, anti-TCF12 antibody, anti-TCF7L2 antibody, anti-TEAD4 antibody, anti-TFAP2A antibody, anti-TFAP2C antibody, anti-THAP1 antibody, anti-TP53 antibody, anti-TRIM28 antibody, anti-TRIM37 antibody, anti-USF1 antibody, anti-USF2 antibody, anti-WHSC1 antibody, anti-WRNIP1 antibody, anti-XRCC4 antibody, anti-ZBTB7A antibody, anti-ZC3H11A antibody, anti-ZKSCAN1 antibody, anti-ZMIZ1 antibody, anti-ZNF143 antibody, anti-ZNF217 antibody, anti-ZNF263 antibody, anti-ZNF274 antibody, anti-ZNF384 antibody, anti-ZZZ3 antibody, anti-YBX1 antibody, anti-SKP1 antibody, anti-SUB1 antibody, anti-PHB2 antibody, anti-SRSF2 antibody, anti-YWHAB antibody, anti-C1QBP antibody, anti-PHB antibody, anti-GMNN antibody, anti-HIRA antibody, anti-PTTG1 antibody, anti-YBX3 antibody, anti-RUVBL2 antibody, anti-GTF3C6 antibody, anti-TAF9 antibody, anti-HNRNPK antibody, anti-TCEB2 antibody, anti-TARDBP antibody, anti-SAP18 antibody, anti-ZRANB2 antibody, anti-TRIP 13 antibody, anti-ILF2 antibody, anti-LMO2 antibody, anti-PSMG4 antibody, anti-PSMC3 antibody, anti-IGF2BP3 antibody, anti-HMGB1 antibody, anti-EID1 antibody, anti-KLF1 antibody, anti-CNOT7 antibody, anti-UBE2K antibody, anti-MYCBP antibody, anti-POLR3K antibody, anti-PA2G4 antibody, anti-HHEX antibody, anti-RPL7L1 antibody, anti-GF11B antibody, anti-POLR3E antibody, anti-TAF11 antibody, anti-CBX1 antibody, anti-ID1 antibody, anti-UHRF1 antibody, anti-ZNRD1 antibody, anti-TDP2 antibody, anti-HDAC3 antibody, anti-HES1 antibody, anti-HES2 antibody, anti-HES3 antibody, anti-HES4 antibody, anti-HES5 antibody, anti-HES6 antibody, anti-HES7 antibody, anti-SUPT16H antibody, anti-ZNF639 antibody, anti-ADNP antibody, anti-GTF2H2 antibody, anti-RBM14 antibody, anti-ALYREF antibody, anti-HTATSF1 antibody, anti-RUVBL1 antibody, anti-WT1 antibody, anti-ZBTB8OS antibody, anti-IREB2 antibody, anti-DCAF6 antibody, anti-HSBP1 antibody, anti-GPN1 antibody, anti-THAP7 antibody, anti-SUV39H2 antibody, anti-MBD2 antibody, anti-RBPJ antibody, anti-TFAM antibody, anti-RFXANK antibody, anti-TMF1 antibody, anti-ZNF281 antibody, anti-KEAP1 antibody, anti-SMARCA5 antibody, anti-CCNE1 antibody, anti-TSFM antibody, anti-KMT2D antibody, anti-POLR2I antibody, anti-MTA1 antibody, anti-NOC2L antibody, anti-TADA1 antibody, anti-CARM1 antibody, anti-TCEB3 antibody, anti-REXO4 antibody, anti-LARP1 antibody, anti-YLPM1 antibody, anti-CIAO1 antibody, anti-GTF2IRD1 antibody, anti-KANK2 antibody, anti-ZFPM1 antibody, anti-GTF2H1 antibody, anti-HNRNPD antibody, anti-CDYL antibody, anti-MTERF2 antibody, anti-ABT1 antibody, anti-NPAT antibody, anti-URI1 antibody, anti-ILF3 antibody, anti-PCGF6 antibody, anti-SCAND1 antibody, anti-NKRF antibody, anti-PCBD1 antibody, anti-E2F2 antibody, anti-SNAPC5 antibody, anti-SSBP4 antibody, anti-CIRBP antibody, anti-AGAP3 antibody, anti-CREBZF antibody, anti-HOXB7 antibody, anti-SHPRH antibody, anti-SMARCD2 antibody, anti-ZFP36L2 antibody, anti-HOXB4 antibody, anti-E4F1 antibody, anti-TAF4B antibody, anti-ECSIT antibody, anti-TOB1 antibody, anti-FUBP1 antibody, anti-MNT antibody, anti-PTGES2 antibody, anti-MAGED1 antibody, anti-ZNF689 antibody, anti-ZNF746 antibody, anti-ZIC2 antibody, anti-MSX1 antibody, anti-ZNF398 antibody, anti-ZBTB9 antibody, anti-GTF3A antibody, anti-NOLC1 antibody, anti-DDX20 antibody, anti-TFCP2 antibody, anti-HMGN5 antibody, anti-NFIA antibody, anti-DEAF1 antibody, anti-GTF2I antibody, anti-ZBTB24 antibody, anti-SS18 antibody, anti-FUS antibody, anti-MLLT10 antibody, anti-TFDP1 antibody, anti-PCID2 antibody, anti-L3MBTL2 antibody, anti-TAF8 antibody, anti-TARBP1 antibody, anti-PIAS2 antibody, anti-MBD1 antibody, anti-ZNF443 antibody, anti-ETV6 antibody, anti-ASB6 antibody, anti-EPC1 antibody, anti-ZNF142 antibody, anti-PIAS4 antibody, anti-TONSL antibody, anti-FOXL2 antibody, anti-EN1 antibody, anti-ZBTB4 antibody, anti-ARID2 antibody, anti-CREM antibody, anti-TAF5L antibody, anti-HTATIP2 antibody, anti-GCFC2 antibody, anti-SMAD1 antibody, anti-RBFOX2 antibody, anti-MECOM antibody, anti-MTERF1 antibody, anti-PIAS3 antibody, anti-NFE2L3 antibody, anti-DMAP1 antibody, anti-ZKSCAN3 antibody, anti-ATF7 antibody, anti-OSR2 antibody, anti-ZBTB45 antibody, anti-TSHZ1 antibody, anti-ZNF174 antibody, anti-PPPIR27 antibody, anti-ZNF83 antibody, anti-TCF4 antibody, anti-ZNF180 antibody, anti-HOXC9 antibody, anti-TAF6L antibody, anti-MED23 antibody, anti-POU4F1 antibody, anti-SOX4 antibody, anti-TGIF2 antibody, anti-MTRF1 antibody, anti-NFIB antibody, anti-ZNF253 antibody, anti-HOXB5 antibody, anti-KIDINS220 antibody, anti-HIVEP1 antibody, anti-PATZ1 antibody, anti-ZMIZ2 antibody, anti-HDAC8 antibody, anti-PQBP1 antibody, anti-ZNF148 antibody, anti-ZBTB47 antibody, anti-BATF3 antibody, anti-MTRFIL antibody, anti-RBL1 antibody, anti-HEXIM2 antibody, anti-MYNN antibody, anti-GTF3C3 antibody, anti-RFX3 antibody, anti-ZEB2 antibody, anti-BPTF antibody, anti-ZMYM5 antibody, anti-RBAK antibody, anti-AFF4 antibody, anti-ZNF19 antibody, anti-SSBP2 antibody, anti-LHX4 antibody, anti-SMARCE1 antibody, anti-ZNF33A antibody, anti-ZFX antibody, anti-SOX7 antibody, anti-ZNF169 antibody, anti-FOXF2 antibody, anti-FLAG tag antibody, anti-His tag antibody, anti-GFP antibody, anti-YFP antibody, anti-RFP antibody, anti-GST antibody, anti-BrdU antibody, anti-V5 tag antibody, anti-Protein C tag antibody, anti-Halo tag antibody, and anti-CRISPR (Cas9) antibody.

In embodiments, reactions may be performed by semi-automated or fully automated systems including microfluidic systems and liquid handling systems.

Using the methods of an embodiment of the invention, to prepare a re-usable single cell using a polyacrylamide nanoscale scaffold, experiments may be repeated multiple times in the same single cell allowing for statistical analysis to validate the results from the single cell. The ability to produce a "re-usable" single cell may overcome issues that currently impair single-cell analysis such as, for example, chromatin immunoprecipitation (ChIP)-based methods. The methods of an embodiment of the invention may provide any one or more of a variety of advantages over ChIP-based methods. For example, using the methods of an embodiment of the invention an artisan may analyze multiple epigenetic modifications, such as DNA methylation, histone acetylation, and histone methylation in the same single cell. In contrast, sequencing using bulk ChIP-seq may require the use of different samples to analyze different genetic modifications, which may prevent reliable analysis at the single-cell level. The methods of an embodiment of the invention may, advantageously, make it possible to apply reproducible controls and statistical analysis to the study of single cells. In contrast, ChIP-based methods lack reproducible controls and power for statistical analysis. Moreover, a single cell prepared by the methods of an embodiment of the invention may, advantageously, be re-usable. In contrast, once a cell is used for one ChIP-seq experiment, it cannot be reused.

Moreover, ChIP-based methods may require destruction of genomic DNA segments between nucleosomes. This loss of large regions of the genome may prevent use of the same sample for epigenetic analysis and genome sequencing. ChIP-based methods may not provide a detailed epigenetic signature in single cells because ChIP-based methods use beads to recover the antibody-target protein complex. Some beads bind non-specifically to nucleosomes due to their large surface area, causing high background or noise, which may prevent identification of smaller peaks from single-cell ChIP analysis.

In an embodiment, the invention may overcome some or all of the shortcomings of ChIP-based methods by maintaining the nucleosome spacing regions when sequencing genomic DNA. The methods of an embodiment of the invention may produce an improved signal to noise ratio in DNA products when sequencing genomic DNA from a single cell. Thus, it may be possible to identify known active promoter regions, with little to no signal in inactive regions, using the inventive methods. As shown in the Examples, using the methods of the invention, it may be possible to identify regions of genomic DNA corresponding to endothelial cell markers, epithelial cell markers, hepatocyte markers, immune cell markers, and stem cell markers, among others.

In an embodiment, the invention relates to methods for sequencing genomic DNA in a single cell. The method comprises annealing to genomic DNA on the single cell a first oligonucleotide primer; wherein the first oligonucleotide primer comprises, in a 5' to 3' orientation, a random nucleotide sequence or specific primers for targeted regions with a first ligation sequence (R); extending the sequence of the first random nucleotide sequence using a first DNA polymerase; binding at least one tagged antibody to an epigenetic modification, or to a nucleotide in the genome; wherein the antibody is tagged with a polynucleotide comprising, in a 5' to 3' orientation, a first polymerase chain reaction (PCR) amplification sequence, an RNA polymerase promoter sequence, a restriction enzyme site sequence, an antibody barcode sequence, and a second ligation sequence (L); joining the second ligation sequence (L) to the first ligation sequence (R) using a ligation adapter and a DNA ligase to create a ligation product; annealing a second oligonucleotide primer to the ligation product, wherein the second oligonucleotide primer comprises in a 3' to 5' orientation a second random nucleotide sequence, a cell barcode sequence, a restriction enzyme site sequence, and a second sequence for PCR amplification; amplifying the ligation product with the annealed second oligonucleotide primer using multiple displacement amplification (MDA) to obtain an MDA-amplified DNA; amplifying the MDA-amplified DNA using PCR, in vitro transcription, and reverse transcription to obtain an amplified genomic DNA fragment; and sequencing the amplified genomic DNA fragment. In some embodiments, the PCR is panhandle PCR. Prior to in vitro transcription, the method may further comprise removing non-specific DNA using DNA digestion. The in vitro transcription may use T7 RNA polymerase, RNA polymerase II, SP6 RNA polymerase, or any RNA polymerase. After in vitro transcription, the method may further comprise purifying RNA using phase separation. In an embodiment of the method, the sequencing is high throughput sequencing of genomic DNA comprising at least one epigenetic modification.

In an embodiment, sequencing genomic DNA in a single cell may comprise collecting genomic DNA of a single cell, amplifying the collected genomic DNA using multiple displacement amplification (MDA) to obtain an MDA-amplified DNA, amplifying the MDA-amplified DNA using PCR, and sequencing the PCR-amplified DNA. In some embodiments, sequencing the genomic DNA in a single cell may comprise sequencing the genomic DNA from a re-usable single cell of some embodiments of the invention. In some embodiments, sequencing the genomic DNA in a single cell comprises using a reducing reagent to degrade the nano-scale polyacrylamide scaffold anchoring the cellular components inside the single cell, removing anchored proteins by treating with Proteinase K for at least about 30 minutes, amplifying the genomic DNA using MDA to obtain MDA-amplified genomic DNA, amplifying the MDA-amplified genomic DNA using PCR to obtain PCR-amplified genomic DNA, and sequencing the PCR-amplified genomic DNA. In some embodiments, the Proteinase K treatment may be for at least about 30 minutes to at least about 3 hours, or any period of time in between.

In an embodiment, the method of sequencing genomic DNA may comprise reducing DNA-protein crosslinks by fixation using a complex of paraformaldehyde and monomer acrylamide; preserving proteins and DNA position by anchoring a polyacrylamide nano-scale scaffold; collecting genomic DNA of a single cell by degrading scaffold polyacrylamide nano-scale scaffold by a reducing agent, and removing proteins by a proteinase; amplifying the single-cell genomic DNA by multiple displacement amplification (MDA) to obtain an MDA-amplified DNA; and amplifying the MDA-amplified DNA using PCR.

In some embodiments, a method for determining the position of an epigenetic modification in a single cell comprises preparing a re-usable single cell as described herein with respect to other aspects of the invention, binding an antibody to the genetic modification, and sequencing the genomic DNA comprising the epigenetic modification using an embodiment of the invention.

Another embodiment of the invention provides a method for determining the position of an epigenetic modification in a single cell. The method comprises preparing a re-usable single cell as described herein with respect to other aspects of the invention. The method further comprises annealing to genomic DNA in the single cell a first oligonucleotide primer, wherein the first oligonucleotide primer comprises, in a 5' to 3' orientation, a first random nucleotide sequence and a first ligation sequence (R). The method may further comprise extending the random nucleotide sequence of the oligonucleotide primer using a first DNA polymerase. The method further comprises binding at least one tagged antibody to an epigenetic modification, wherein the antibody is tagged with a polynucleotide comprising, in a 5' to 3' orientation, a nucleotide sequence for panhandle PCR amplification, an RNA polymerase promoter sequence, a restriction enzyme site sequence, an antibody barcode sequence, and a second ligation sequence (L). The method may further comprise joining the ligation sequence (L) to the ligation sequence (R) using a ligation adapter and a DNA ligase to create a ligation product. The method further comprises annealing a second oligonucleotide primer to the ligation product, wherein the second oligonucleotide primer comprises, in a 3' to 5' orientation, a second random nucleotide sequence, a cell barcode sequence, a restriction enzyme site sequence, and a nucleotide sequence for PCR amplification. The method further comprises amplifying the ligation product with the annealed second oligonucleotide primer using multiple displacement amplification (MDA) to obtain an MDA-amplified DNA. The method may further comprise amplifying MDA-amplified DNA using PCR to obtain a PCR-amplified product. The method may further comprise converting the PCR-amplified product to RNA using RNA polymerase. In some embodiments, the PCR amplified product converted to RNA contains the T7 promoter sequence, and is converted to RNA using T7 RNA polymerase and in vitro transcription. The method may further comprise removing DNA using DNA digestion. The method may further comprise purifying the RNA using phase separation or other RNA purification method. The method may further comprise converting the purified RNA containing a nucleotide sequence of the second oligonucleotide primer using a primer for reverse transcription containing a partial sequence of the second oligonucleotide primer. The method may further comprise synthesizing a second strand of the converted DNA using a primer for the restriction enzyme site and the scaffold DNA sequence. The method may further comprise sequencing the resulting DNA product generated, which contains an antibody bar code and a cell barcode.

In an embodiment of the invention, the method may comprise amplifying the MDA-amplified DNA using PCR, converting PCR-amplified DNA containing the T7 promoter sequence to RNA using T7 RNA polymerase in vitro transcription; removing DNA by DNase digestion; purifying the RNA using phase-separation methods; converting the purified RNA containing sequence of the second oligonucleotide primer to DNA using a primer of reverse transcription containing a partial sequence of the second oligonucleotide primer; synthesizing second strand of the converted DNA using a primer for the restriction enzyme site and the scaffold DNA sequence; and sequencing the generated genomic DNA fragment containing an antibody barcode and cell barcode.

In some embodiments, the PCR may use Taq polymerase; or the PCR may be real-time PCR, nested PCR, multiplex PCR, quantitative PCR, arbitrary primed PCR, or panhandle PCR. In some embodiments, the restriction enzyme site may be a BciVI restriction enzyme site.

In an embodiment of the invention, the method may further comprise binding a control antibody to the single cell. In an embodiment of the invention, the method further comprises incubating the single cell simultaneously in the presence of the control antibody and the antibody specific for at least one epigenetic modification.

The epigenetic modification may be as described herein with respect to other aspects of the invention.

The methods of an embodiment of the invention may allow for the determination of one or more modifications in the genome, epigenome, and transcriptome at a single-cell level. By preparing a re-usable single cell, it may be possible to determine multiple modifications (e.g., more than one modification) in the genome, epigenome, or transcriptome in the same single cell. The methods of an embodiment of the invention may be widely applicable to research of the physiology of cell components and tissues of the mature individual (i.e., once development has ended in the individual). The methods of an embodiment of the invention may also be useful in the study of diseases in which different cells contribute to the disease in a different manner. For example, cancer is a disease of individual cells which may markedly differ from each other. Thus, the methods of the invention may be useful in cancer research. The methods of an embodiment of the invention may allow for the study of individual cells and analyze the data statistically, thereby solving the issues presented by this heterogeneity. The methods of an embodiment of the invention may also be useful for the development of new therapeutics that target epigenetic alterations at a single cell level. The methods of an embodiment of the invention may be useful in arriving at treatment decisions based on a new understanding of cell heterogeneity, particularly in the context of emerging drug resistance to treatment.

As used herein, "annealing cycle" and "heating/cooling cycle" are used interchangeably. These terms refer to cycles of heating and cooling. For example, the heating and cooling may be used for annealing a DNA primer, or for sequencing genomic DNA using PCR, among others. A re-usable single cell may provide the ability to repeat experiments using the same single cell with controls and to perform statistical analysis on the results obtained from the single cell. Until now, it has not been possible to perform statistical analysis on the results from a single cell because it has not been possible to use the same cell for more than one experiment.

In an embodiment, the invention provides a method for analyzing in a single cell at least one of the genome, epigenome, and transcriptome in a single cell, the method comprising preparing a nano-scale scaffold to anchor the single cell cellular components inside the single cell as described herein with respect to other aspects of the invention; and detecting the presence of a modification in at least one of the genome, epigenome, and transcriptome in the single cell. In some embodiments, the method for analyzing in a single cell at least one of the genome, epigenome, and transcriptome comprises detecting a modification on at least one of genomic DNA, DNA methylome, DNA hydroxyl methylome, histone modification, binding of histone modifier, DNA binding protein, and binding of RNA polymerase, as described herein with respect to other aspects of the invention. In some embodiments, the method for analyzing at least one of the genome, epigenome, and transcriptome in the single cell comprises using an antibody which specifically recognizes a genome modification, an epigenome modification, or a transcriptome modification. In some embodiments, the method for analyzing at least one of the genome, epigenome, and transcriptome in the single cell further comprises using a ligation adapter.

In an embodiment, the invention relates to a method for determining the location of an epigenetic modification in a genome of a single cell, comprising binding an antibody to the epigenetic modification on the genome; and sequencing a portion of the genome of the single cell comprising the epigenetic modification, to determine the location of the epigenetic modification on the genome. The epigenetic modification may be located in the region where the antibody bound. In some embodiments, the invention relates to a method for determining the location of epigenetic modification in a genome of a re-usable single cell, comprising preparing a re-usable single cell according to any of the methods described herein with respect to other aspects of the invention; binding an antibody to the epigenetic modification on the genome; and sequencing a portion of the genome of the single cell comprising the epigenetic modification, to determine the location of the epigenetic modification on the genome.

In some embodiments, a control antibody and an antibody specific for at least one epigenetic modification are used simultaneously in the same cell. In some embodiments, multiple types of epigenetic modifications are identified in the same single cell. In some embodiments, the antibody is selected from anti-5-methylcytosine antibody, anti-5-hydroxymethylcytosine antibody, anti-histone H3K27ac antibody, anti-histone H3K27me3 antibody, anti-histone H3K9ac antibody, anti-histone H3K9me3 antibody, anti-transcription factor antibody, anti-Med1 antibody, anti-HP1 antibody, anti-HDAC1 antibody, anti-P300 antibody, anti-STAT1 antibody, and anti-RNA polymerase II antibody.

In an embodiment, the invention relates to a method for identifying the epigenetic pathway to cancer. The method comprises determining the position of at least one epigenetic modification in one or more single cells using any of the methods described herein with respect to other aspects of the invention. In an embodiment, the invention relates to a method for identifying the epigenetic pathway to cancer, including but not limited to multiple myeloma, colon cancer, cervical cancer, or Acute Myelogenous Leukemia (AML). The method comprises determining the position of at least one epigenetic modification in one or more single cells using any of the methods described herein with respect to other aspects of the invention, where the patient has a history of one or more of gammopathies, intestinal polyps, cervical dysplasia, Myelodysplastic Syndromes (MDS), pre-cancerous lesions or conditions, including (but not limited to) cirrhosis, liver steatosis, Crohn's disease, ulcerative colitis, gastritis (atrophic), ductal in situ carcinoma, oral leukoplakia, skin T-cell infiltration syndromes, and bladder carcinoma in situ that developed to cancer. In some embodiments, the method for identifying the epigenetic pathway to cancer, including but not limited to Acute Myelogenous Leukemia (AML) comprises determining at least one epigenetic modification in one or more single cells using the method of an embodiment of the invention, where the patient has a history of pre-neoplastic lesions, including but not limited to, Myelodysplastic Syndromes (MDS) that developed to AML, colonic polyps leading to colon cancer, or cervical epithelial dysplasia leading to cervix cancer. In some embodiments, the invention relates to a method for mapping the genetic evolution from pre-neoplastic lesions to cancer, including but not limited to, MDS to AML, colonic polyps to colon cancer, or cervical dysplasia to cancer of the cervix by determining the position of at least one epigenetic modification in one or more single cells using any of the methods described herein with respect to other aspects of the invention, wherein the epigenetic modification identifies the founder cell among cancer cells. In some embodiments, the invention provides a method for identifying a cell of origin of cancer, including but not limited to AML among MDS cells, colon cancer cells within colonic polyps, carcinoma cells among dysplastic epithelial cells based on determining the position of at least one epigenetic modification in one or more single cells using any of the methods described herein with respect to other aspects of the invention.

In some embodiments, the methods described herein may be used as high throughput methods. In an embodiment, the invention provides a method for directing early treatment of cancer that targets individual cancer-prone cells identified in pre-neoplastic lesions using any of the methods described herein with respect to other aspects of the invention, where the neoplastic lesions are likely capable of evolving into cancer. In an embodiment, the invention provides a method for identification of single cancer cells responsible for the development of resistance to treatment, prior to clinical detection of resistance. In an embodiment, the invention provides a method for mapping the evolution of resistance to cancer treatment. In an embodiment, the invention provides for a method for directing treatment to prevent the occurrence of resistance to treatment. In an embodiment, the invention provides for a method for directing treatment changes once individual resistant cells are identified within a cancer.

In an embodiment, the invention provides a kit for preparing a re-usable single cell. In some embodiments the kit comprises formaldehyde and an acrylamide monomer, acrylamide-N,N'-bis(acryloyl)cystamine or acrylamide-bisacrylamide, TEMED in mineral oil, and instructions to create a scaffold to prepare a re-usable single cell. In some embodiments, the kit for preparing a re-usable single cell of an embodiment of the invention further comprises at least one antibody to at least one epigenetic modification; and instructions for using the at least one antibody to determine the location on the genome of the epigenetic modification.

An embodiment of the invention provides an automated system for carrying out the inventive method, wherein the system forms the re-usable single cell and analyzes sequencing results.

In an embodiment of the invention, the method is automated.

Another embodiment of the invention provides a computer program for customizing the analysis of sequencing results obtained from the inventive method.

In an embodiment of the invention, the method identifies cancer stem cells within a tumor or a tissue in vitro.

In an embodiment of the invention, the method identifies cancer cells with trans differentiation potential in vitro.

In an embodiment of the invention, the method identifies mutant/altered cell proliferation that confers resistance to treatment.

In an embodiment of the invention, the method identifies rare cancer cell populations and the method further comprises guiding cancer treatment based on the rare cancer cell populations.

In an embodiment of the invention, the method predicts metastatic potential of individual cancer cells in vitro.

In an embodiment of the invention, the method detects rare cells in vitro, wherein the rare cells confer a tumor microenvironment with pro-tumorigenic or anti-tumorigenic functions.

In an embodiment of the invention, the method allows tailored therapy for resistant cell populations.

Another embodiment of the invention provides a method of designing new drugs based on the identification of subsets of cancer cells with specific changes amenable to drug targeting, wherein the subsets of cancer cells are identified by the inventive method.

Another embodiment of the invention provides a method of designing a combination of drugs that target specific cells within a cancer, wherein the cancer is not targeted by current treatments, the method comprising identifying the specific cells by the inventive method.

Another embodiment of the invention provides a method for identifying single cells for production of biologically active agents, the method comprising identifying single cells by the inventive method.

Another embodiment of the invention provides a method for identifying/distinguishing new cell subpopulations, the method comprising identifying/distinguishing new cell subpopulations by the inventive method.

Another embodiment of the invention provides a method of identifying a role of sub clonal populations in diseases other than cancer, the method comprising identifying sub clonal populations by the inventive method.

The following examples further illustrate the invention but, of course, should not be construed as in any way limiting its scope.

Example 1

This example demonstrates a method of preparing a re-usable single cell by anchoring the cellular components inside the single cell with a polyacrylamide nano-scale scaffold.

Figure 1:
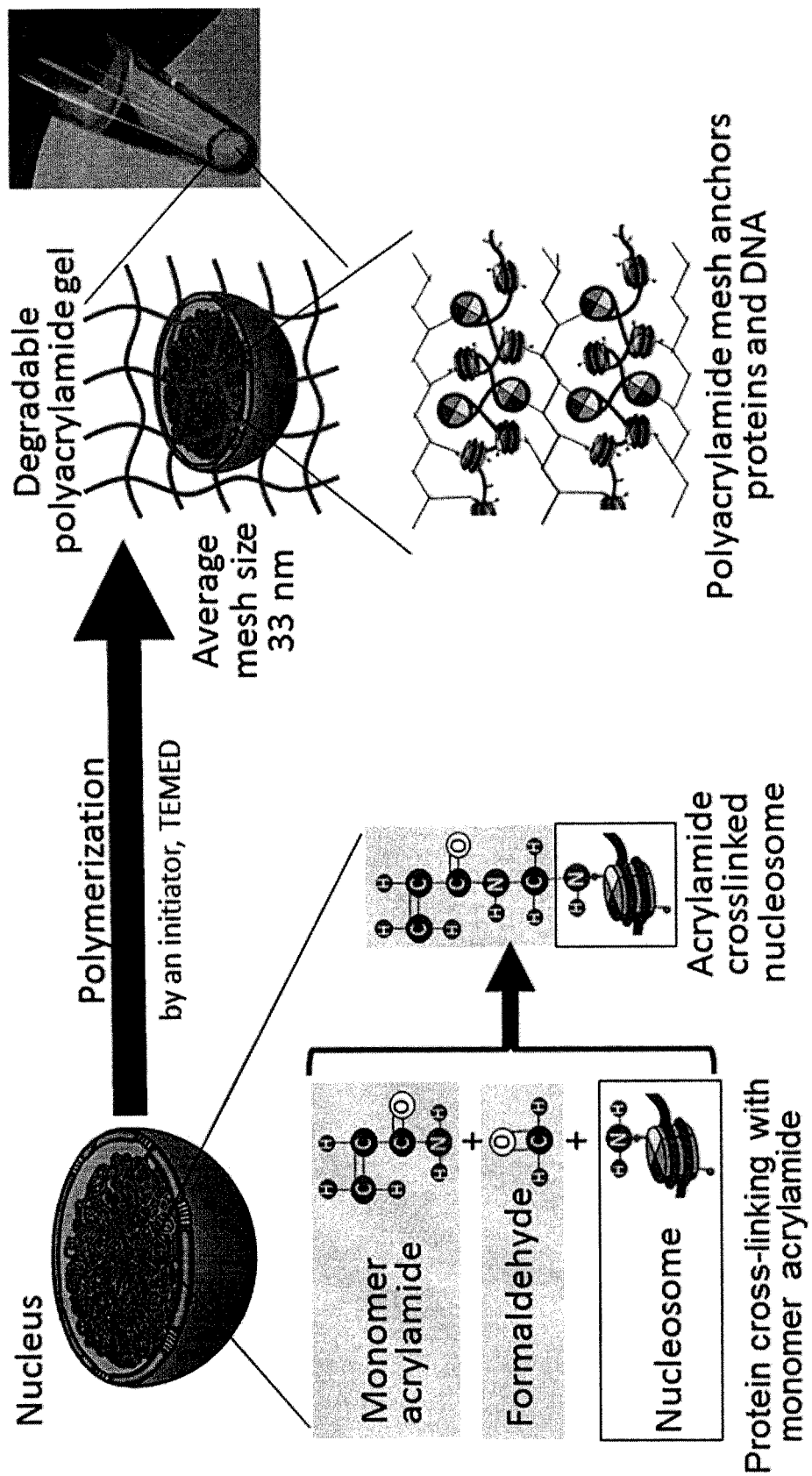
FIG. 1 is a schematic illustrating a method of preparing a re-usable single cell using a polyacrylamide nano-scale scaffold to anchor the cellular components inside the single cell according to an embodiment of the invention.

A diagram illustrating an embodiment of the inventive method for preparing a polyacrylamide nano-scale scaffold of the invention is provided in FIG. 1. To prepare the polyacrylamide nano-scale scaffold, $1 \times 10^6$ MS1, or K562 cells were dispersed in a phosphate-buffered saline solution comprising 4% formaldehyde (PFA) and either 1%, 4% 5%, 10%, 20% acrylamide, or 28% acrylamide. The dispersed cells were held for one hour on ice to allow the PFA and acrylamide to bind to the cellular proteins, followed by washing the dispersed cells with Tris buffered saline (TBS) solution to remove free PFA and free acrylamide. The cells were pelleted by centrifugation, the TBS was removed, and the cells were resuspended in a solution containing 1% sodium ammonium persulfate, and 4% acrylamide-bisacrylamide or 4% acrylamide-N,N'-bis(acryloyl) cystamine in TBS. The acrylamide to bisacrylamide ratio used was 16.667:1, and the percentage of bisacrylamide used was 6% of the acrylamide. The suspended cells were transferred into mineral oil containing 0.2% N,N,N',N'-tetramethylethylenediamine (TEMED) and the acrylamide allowed to polymerize.

This method resulted in the formation of a polyacrylamide nano-scale scaffold. When analyzed, the polyacrylamide nano-scale scaffold had an average mesh size of about 33 nm. As seen below, the polyacrylamide nano-scale scaffold retained cellular components inside the cell even after treating the cell with multiple heating and cooling cycles. Thus, more than one assay may be performed on each single cell, creating a re-usable single cell.

Example 2

This example demonstrates that cellular components anchored by the polyacrylamide nano-scale scaffold are accessible to antibodies.

K562 cells were embedded in a polyacrylamide nano-scaffold prepared utilizing 20% acrylamide and 4% acrylamide-bisacrylamide, as described in Example 1. Once the polyacrylamide nano-scale scaffold was polymerized, the oil was removed, and the cells were incubated in 1% TRITON X-100 ("the surfactant" Dow Chemical Company, Midland, Mich.) for at least 15 minutes. Incubation in the presence of surfactant permeabilizes the cells and allows buffers and reagents to enter the cells. The cells were then immersed in annealing buffer (20 mM Tris-HCl, pH 8.8, 10 mM (NH$_4$)$_2$SO$_4$, 10 mM KCl, 0.1% surfactant) and 0.2 to 20 µM of the first oligonucleotide primer. The cells were then heated at 94° C. for 3 minutes. To avoid non-specific binding of antibodies the cells were transferred to 12.5 mM EDTA containing 2.5% bovine serum albumin (BSA) and 1% surfactant. The cells were incubated for more than one hour on ice. The cells were then incubated for two days in the presence of an anti-H3K9ac rabbit polyclonal antibody (Active Motif, Carlsbad, Calif., Cat #39317, Lot #1008001) which recognizes the acetylation of Lys 9 on histone 3. After removing unbound antibody by washing the cells with washing buffer (2.5% BSA, 300 mM NaCl, 20 mM Tris-HCl pH 8.8, 10 mM (NH$_4$)$_2$SO$_4$, 10 mM KCl, 0.1% surfactant), the cells were incubated with an anti-rabbit IgG secondary antibody conjugated to ALEXA FLUOR 488 dye ("the dye"; Molecular Probes, Inc., Eugene, Oreg.) obtained from Thermo Fisher Scientific (Waltham, Mass.; Cat #R37118), and 4',6-diamidino-2-phenylindole, dihydrochloride (DAPI). Aliquots of cells were removed at the time of addition of the secondary antibody (t=0), and 1 hour, 2 hours, 4 hours, 8 hours, and 16 hours after addition of the secondary antibody. The cells in each aliquot were washed briefly with TBS containing 0.1% surfactant and fixed again with 4% PFA in PBS. Images of the cells were obtained using a fluorescence microscope to view both, the dye and the DAPI.

Figure 2:
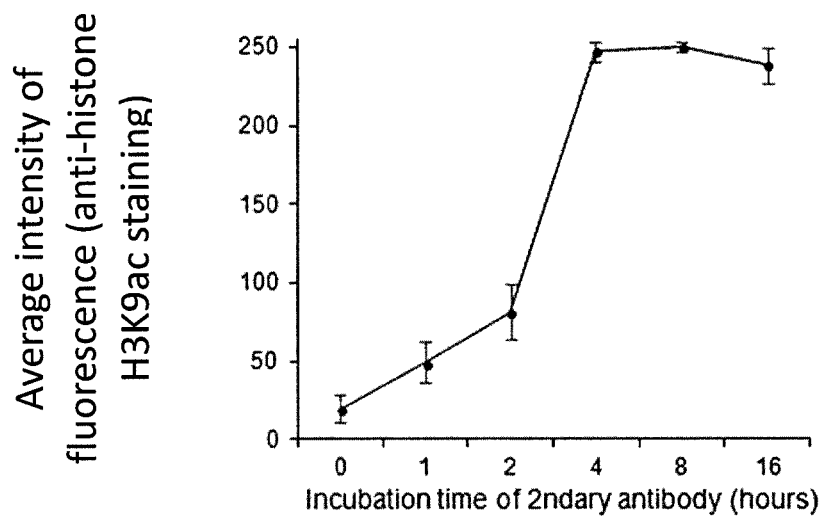
FIG. 2 is a graph showing a time course of the average fluorescence intensity of cells treated with an anti-histone H3K9ac antibody and an anti-rabbit secondary antibody labeled with the dye. Staining intensity measured by confocal microscopy.

DAPI is a fluorescent stain that binds strongly to A-T regions in DNA and is commonly used to locate the nucleus of cells when using fluorescence microscopy. Even after only one hour of incubation in the presence of the secondary antibody and DAPI, signal for the fluorescence of the dye and DAPI were detected in the same cells. These results indicate that cellular components anchored with a polyacrylamide nano-scaffold were accessible to antibodies. FIG. 2 depicts a graph of a time course of the average intensity of the fluorescence of the dye in cells treated with anti-histone H3K9ac antibody and a secondary antibody labeled with the dye. The graph shows that incubation in the presence of secondary antibody for four (4) hours yields the highest dye signal.

Example 3

This example demonstrates that the polyacrylamide nano-scale scaffold retains proteins inside a single cell even after repeated heating and cooling cycles, thereby generating a "re-usable" single cell.

The experiments in this Example were performed to determine the effect of the polyacrylamide nano-scale scaffold on the retention of proteins in a single cell. A polyacrylamide nano-scaffold was prepared using $1\times10^6$K562 cells utilizing methanol, 4% formaldehyde (PFA), 4% PFA with 1% acrylamide, 4% PFA with 5% acrylamide, 4% PFA with 10% acrylamide, 4% PFA with 20% acrylamide, or no fixative, and 4% acrylamide-bisacrylamide as described in Example 1. The cells were washed once with hydrogel solution (3.88% acrylamide, 0.12% bis(acryloyl)cystamine, 1% ammonium persulfate, and 1× phosphate buffered saline (PBS)). Single cells were suspended in hydrogel solution at 3 µl per cell. Single cells (3 µl of cell suspension) were transferred into a PCR tube containing 0.2% TEMED in mineral oil, and incubated for 1 hour at room temperature to polymerize the acrylamide. The mineral oil was removed by pipetting. To each tube containing cells embedded in polyacrylamide gel, 100 µl of annealing buffer were added. After incubation of the cells on ice for 30 minutes, the supernatant was collected and the cells were resuspended in 100 µl annealing buffer. The cells were heated at 94° C. for 3 minutes, cooled to 4° C. for 2 minutes, followed by incubation in ice for 30 minutes (which provides one heating/cooling cycle). Each heating/cooling cycle was repeated for 100 times. Samples were removed after each cycle. The results are depicted in FIG. 3.

FIG. 3 shows that when no fixative was used, less than about 20% of cellular proteins remained after addition of the annealing buffer. Less than about 10% of cellular proteins remain after one heating/cooling cycle. When the cells were fixed in methanol, less than about 40% of cellular proteins remained after addition of the annealing buffer. Less than about 30% of cellular proteins remained after 100 heating/cooling cycles. When the cells were fixed with formaldehyde alone, less than about 90% of cellular proteins remained after addition of the annealing buffer. Less than about 75% of cellular proteins remained after 100 heating/cooling cycles. When the cells were fixed with formaldehyde and acrylamide (formaldehyde crosslinks monomer acrylamide to protein amino groups), about 100% of the cellular proteins remained after addition of the annealing buffer regardless of the amount of acrylamide used. Small differences in retention were apparent for the different amounts of acrylamide used as the number of heating/cooling cycles increased. Similar results as those shown in FIG. 3 were obtained when using 4% acrylamide-N,N'-bis (acryloyl) cystamine during the preparation of the polyacrylamide nano-scale scaffold.

In summary, after 10 heating/cooling cycles, unfixed cells lost 91.1% of their total protein content. Cells fixed with formaldehyde and no acrylamide lost 56.9% of their protein content. After 10 heating/cooling cycles, cells fixed with formaldehyde and no acrylamide lost 53.4% of RNA polymerase II (Pol II) protein, while the cells fixed with the polyacrylamide nano-scale scaffold lost only 6% of their Pol II protein. This demonstrates the polyacrylamide nano-scale scaffold preserves cellular proteins in the single cell even after repeated experiments. The single cell is then a "re-usable" single cell which may be used for multiple experiments.

Sequencing to determine the location of epigenetic modifications was obtained using re-usable single cells embedded in a polyacrylamide nano-scale scaffold prepared with 4% acrylamide-bis(acryloyl)cystamine or with 4% acrylamide-bis-acrylamide. The results obtained with both nano-scale scaffolds were similar. These results suggest that 4% acrylamide-bis(acryloyl)cystamine and with 4% acrylamide-bis-acrylamide can retain the proteins inside the re-usable single cell during repeating annealing steps. The difference between bis(acryloyl)cystamine and bis-acrylamide is the presence or absence of a disulfide bound in the center of the chemical structure, which will not affect polymerization of acrylamide or protein retention.

Example 4

This example demonstrates that amplifiable DNA is recovered after using a reducing agent for removing the polyacrylamide nano-scale scaffold of an embodiment of the invention.

The experiments in this Example were performed to determine the effect of the polyacrylamide nano-scale scaffold on the retention of amplifiable DNA. A polyacrylamide nano-scaffold was prepared using $1\times10^6$K562 cells utilizing methanol, 4% formaldehyde (PFA), 4% PFA with 1% acrylamide, 4% PFA with 5% acrylamide, 4% PFA with 10% acrylamide, 4% PFA with 20% acrylamide, or no fixative, and 4% acrylamide-N,N'-bis(acryloyl) cystamine as described in Example 1.

The polyacrylamide nano-scale scaffold was degraded by incubating the cells in 100 mM dithiothreitol (DTT) for 60 minutes. Proteins were digested with the addition of 0.8 mg/ml proteinase K, 0.1% surfactant, 10 mM ethylenediaminetetraacetic acid (EDTA) in TBS to the cells. After incubating the cells for at least 30 minutes, proteinase K was heat-inactivated by incubating the cells at 94° C. for 10 minutes. Amplifiable genomic DNA was measured by performing quantitative polymerase chain reaction (Q-PCR) using SYBR GREEN cyanine dye ("the cyanine dye;" Molecular Probes Inc., Eugene Oreg.) and primers for chromosome 1 (chr1:175727200+175727264). The results were plotted in reference to data obtained from cells treated without fixative. As seen in FIG. 4, about less than 4% of amplifiable DNA was recuperated when the cells were fixed with 4% formaldehyde in the absence of acrylamide. Even less genomic DNA was recuperated when the polyacrylamide nano-scale scaffold was prepared with 4% formaldehyde and 1% acrylamide, 4% formaldehyde and 5% acrylamide, or 4% formaldehyde and 10% acrylamide. Surprisingly, over 10% of the amplifiable DNA was recovered when a polyacrylamide nano scale scaffold was prepared using 4% formaldehyde and 20% acrylamide.

These results show that it is possible to recover amplifiable DNA from re-usable single cells prepared with the polyacrylamide nano-scale scaffold of an embodiment of the invention. The polyacrylamide nano-scale scaffold is degradable with reducing agents such as DTT. Thus, it is possible to recover amplifiable DNA after performing epigenetic analysis on a single cell having its cellular components anchored with a polyacrylamide nano-scale scaffold. The single cell is a "re-usable" single cell which may be used for multiple experiments.

Example 5

This example demonstrates a method for sequencing genomic DNA and acquiring locational information of antibodies on the genome to identify the location of histone modifications, DNA modifications and bound proteins on the genome in single cells. In this method, antibodies are bound to epigenetic modifications, and the position of the epigenetic modifications is determined based on the genomic sequence close to the bound antibody.

The steps used for sequencing genomic DNA using the method of an embodiment of the invention are depicted in FIGS. 5A-5I. An oligonucleotide primer comprising 8 random nucleotides (NNNNNNNN is SEQ ID NO: 1) and a first ligation sequence (R) was annealed to the genomic DNA in the cell. The random nucleotides of the oligonucleotide primer were extended using DNA polymerase to stabilize the oligonucleotide primer bound to the genomic DNA. The cell was incubated in the presence of an anti-H3K27ac antibody (which binds to the acetylation at the 27$^{th}$ lysine of histone H3) either alone or in the presence of a control antibody to bind the antibody to the epigenetic modification. The control antibody was a rabbit IgG purified from the serum of a non-immunized rabbit. A polynucleotide comprising, in a 5' to 3' orientation, a nucleotide sequence for Panhandle PCR amplification, a T7 RNA polymerase promoter sequence, a BciVI restriction enzyme site sequence, an antibody barcode sequence, and a second ligation sequence (L, which is the left part of a PAIR end Read 1 sequencing primer). A ligation adapter and DNA ligase were then used to join the ligation sequence R to the ligation sequence L to create a ligation product. A second oligonucleotide primer (NNNNNNNN is SEQ ID NO: 1) was annealed to the ligation product. The second oligonucleotide primer comprises in a 3' to 5' orientation a second random nucleotide sequence, a cell barcode sequence, a BciVI restriction enzyme site sequence, and a nucleotide sequence for panhandle PCR amplification. The ligation product was amplified with the annealed second oligonucleotide primer using multiple displacement amplification (MDA) and *Bacillus stearothermophilus* DNA Polymerase (Bst DNA polymerase) to obtain an MDA-amplified DNA. Panhandle PCR was used to amplify the MDA-amplified DNA to obtain a panhandle PCR product. The panhandle PCR product was converted to RNA using T7 RNA polymerase. The RNA was separated from DNA using DNA digestion, and the RNA was purified using phase separation. The RNA products containing a nucleotide sequence for panhandle PCR amplification at the 3' end were converted to DNA products using reverse transcription. The resulting DNA products were sequenced using a sequencer.

The control antibody and the specific antibody were labeled using barcoding. In some cases a control antibody was used along with an antibody to a selected epigenomic modification. This allowed for the performance of statistical analysis to distinguish signal from noise at a single cell level.

Example 6

This example demonstrates that the results obtained when using the methods described herein are superior when compared with other methods currently used in epigenomic analysis.

A polyacrylamide scaffold was produced to prepare re-usable K562 cells following the methods of Example 1. Briefly, cells were fixed with 4% PFA and 4% acrylamide, and polymerized with 4% acrylamide/bis(acryloyl)cystamine, 1% ammonium persulfate in mineral oil containing 0.2% TEMED. An anti-H3K27ac antibody (which binds to the acetylation at the 27$^{th}$ lysine of histone H3) and a control antibody (normal rabbit IgG purified from non-immunized rabbit serum) were used to sequence single cell genomic DNA following the method described in Example 5. Using these methods in a single K562 cell, portions of the genome were successfully sequenced 14.0 million times, with 91.5% of these sequences having a unique DNA sequence. In comparison, single-cell chromatin immunoprecipitation and parallel sequencing (scChIP-seq) is reported to acquire an average of 2,400 sequencing reads per single cell (Rotem et al., Nature Biotechnol. 33: 1165-1172 (2015)). Thus, the method described in Example 5 is capable of producing 3,083-fold more sequencing reads than currently known methods.

Chromatogram regions obtained from a re-usable single cell whose genomic DNA was sequenced using the methods described in Example 5 were compared to chromatogram regions obtained from using bulk ChIP-seq. Results of chromatogram regions corresponding to known active promoters such as U7 snRNP, BMI1 proto-oncogene, BCLAF1, BCL2 associated transcription factor 1, and the inactive promoter region of the LCE1 family of genes are described below.

The U7snRNA56 is an RNA molecule and a component of the small nuclear ribonucleoprotein complex (U7 snRNP) which is required for histone pre-mRNA processing. The chromatin region corresponding to U7 small nuclear RNA 56 resulting from both methods were very similar. The anti-H3K27ac antibody showed mainly one concentration of peaks at the U7 snRNP active promoter region. With both methods there were only very small peaks visible for the control antibody.

BMI1 is a component of the Polycomb group (PcG) multiprotein PRC-like complex. This complex class is required to maintain the transcriptionally repressive state of many genes. The chromatin region corresponding to BMI1 proto-oncogene were different for both methods. Using the single-cell method of an embodiment of the invention the anti-H3K27ac antibody produced mainly a concentration of peaks at the active promoter regions. Using bulk ChIP-seq the anti-H3K27ac antibody produced larger peaks, both in the active promoter regions and in other regions of the chromatin. Only one small peak was visible when using the single-cell method of an embodiment of the invention and the control antibody. Using bulk ChIP-seq the control antibody produced small, but visible, peaks throughout the chromatin region.

BCLAF1 is also referred to as BCL2 associated transcription factor 1. This gene encodes a transcriptional repressor that interacts with several members of the BCL2 family of proteins. The peak patterns resulting from both methods were similar. Using the single-cell method of an embodiment of the invention the anti-H3K27ac antibody produced a tall peak in the active promoter region, and a couple of small peaks throughout the chromatin region. Using bulk ChIP-seq the anti-H3K27ac antibody showed three tall peaks at the active BCLAF1 promoter region. Using the single-cell method of an embodiment of the invention the control antibody produced one small peak in the active promoter region. Using bulk ChIP-seq the control antibody did not produce any detectable peaks. The fact that the control antibody produces a much smaller peak in the chromatogram compared to the peak produced by the anti-H3K27ac antibody when using the single re-usable cell is an indication that the chromatogram peak seen with anti-H3K27ac is a specific signal.

Syndecan-4 is a protein that in humans is encoded by the SDC4 gene. Syndecab-4 is a ubiquitous cell surface proteoglycan which mediates numerous cellular processes through signaling pathways that affect cellular proliferation. Using the single-cell method of an embodiment of the invention the anti-H3K27ac antibody produced a large peak at the active SDC4 promoter region, and some very small peaks interspaced throughout. Using bulk ChIP-seq the anti-H3K27ac antibody produced many peaks throughout the chromatin region, with some peaks larger than those appearing at the active promoter region. Using the single-cell method of an embodiment of the invention the control antibody produced one very small peak at the active promoter region. Using bulk ChIP-seq the control antibody produced many small peaks throughout the entire chromatogram region. A smaller peak in the chromatogram using the control antibody is an indication that the chromatogram peak seen with anti-H3K27ac is a specific signal.

The LCE1 family genes are part of the Late Cornified Envelope (LCE) gene cluster within the epidermal differentiation complex (EDC). These genes are expressed relatively late during fetal assembly of the skin cornified envelope. Using the single-cell method of an embodiment of the invention the anti-H3K27ac antibody produced very small peaks in this region of the chromatogram. Using bulk ChIP-seq the anti-H3K27ac antibody and the control antibody small peaks throughout this chromatogram region. Using the single-cell method of an embodiment of the invention the control antibody produced no peaks on this chromatogram region. Very small peaks visible in the chromatograms obtained with both antibodies and both methods indicate inactive states in the LCE1 family genes.

The peak patterns obtained with the methods of an embodiment of the invention are similar to those obtained with ChIP-seq in regions corresponding to active promoters and to inactive regions. This data supports the idea that the methods of an embodiment of the invention can distinguish active regions from inactive regions in the chromosome. In known inactive regions both, the methods of the invention and bulk ChIP-seq, showed little or no peaks on the chromatin regions. The identification of peaks in the same positions of the chromosome as those seen when using bulk ChIP seq is an indication that the methods of an embodiment of the invention can be used to determine the position of histone modifications at the single cell level.

Example 7

This example demonstrates that the single-cell method of an embodiment of the invention showed an improved performance when compared to scChIP-seq.

Multiple displacement amplification (MDA) amplifies the ligation products of the antibody probe and $1^{st}$ random primer, and also genomic DNA, which does not contain sequences of panhandle PCR, T7 promoter and antibody barcode (non-specific products). As seen in FIG. 6, the byproducts normally present during MDA are reduced when amplifying and sequencing genomic DNA using both in vitro transcription and reverse transcription as described in Example 5. A graph showing the amount of products in ng/µl total DNA is shown in FIG. 6. This graph shows that the amount of DNA products containing antibody barcodes of control IgG and anti-H3K27ac antibody, which are quantitated by real-time PCR using PCR primers specific for antibody barcode with standard curves of synthesized DNA containing antibody barcode of control IgG and anti-H3K27ac antibody. The quantitation was performed for products after MDA and panhandle PCR reaction (MDA/pPCR products), after MDA, pPCR and PCR reaction with P5 and P7 primers (MDA/pPCR/P5+P7 products) and after MDA, pPCR, In vitro transcription, reverse transcription and PCR with P5 and P7 primers (MDA/pPCR/IVT/RT/P5+P7 PCR products). The amount of non-specific products, products containing the antibody barcode of control IgG, or products containing the antibody barcode of anti-H3K27ac antibody are shown in FIG. 6. As seen in FIG. 6, the methods of an embodiment of the invention reduce the amount of non-specific products and products derived from control antibody, while increasing the amount of products derived from anti-H3K27ac antibody.

As seen in FIG. 6, the products obtained when amplifying genomic DNA obtained from MDA using antibody-specific primers provides 1 µg MDA/pPCR products containing 0.16 ng of DNA products having an antibody barcode of control IgG, 1.77 ng of DNA products having an antibody barcode of anti-H3K27ac antibody, and 998.7 ng of non-specific products, which do not contain antibody barcode. Addition of amplification using the P5 and P7 primers decreases the non-specific products to 222.50 ng/l g total DNA, increases the control IgG-derived products to 78.84 ng/µg total DNA, and increases the anti-H3K27ac-derived products to 698.66 ng/µg total DNA. Addition of in vitro transcription and reverse transcription to the method decreases the non-specific products to 34.72 ng/µg total DNA, decreases the control IgG-derived products to 40.48 ng/µg total DNA, and increases the anti-H3K27ac-derived products to 924.80 ng/µg total DNA.

Sequencing the DNA products using the methods described in Example 5 reduces the non-specific reactions to 4.28%. FIG. 7A and FIG. 7B show results from an experiment in which 14,006,322 total reads were obtained. As seen in FIG. 7A, when sequencing per the methods described in Example 5 the percentage of sequenced reads that do not contain a genomic sequence is about 45% in control-IgG derived products and is less than about 30% in anti-H3K27ac antibody derived products. As seen in FIG. 7B, about 30% of DNA sequences of control-IgG derived products were not mapped to the genome, and less than 25% of DNA sequences of anti-H3K27ac antibody derived products were not mapped to the genome. These results indicate that association of antibody proximal to the chromosome increases acquisition of genomic sequences as an indicator of locational information of antibodies on the genome.

Example 8

This example further demonstrates that peak patterns obtained using the methods of an embodiment of the invention are useful for determining the location of at least one epigenome modification.

In this example, regions of chromosomes corresponding to sequences of endothelial cell markers, epithelial cell markers, hepatocyte markers, immune cell markers, muscle cell markers, neural cell markers, and ES/iPS cells are shown. These peak patterns were obtained using a paraformaldehyde-fixed single cell and an anti-H3K9ac antibody or a control antibody. Peak patterns were obtained using the methods of Example 5, or using bulk ChIP-seq.

Regions of chromosomes containing genes for the endothelial cell markers VE-cadherin, CD31, Tie2, VEGFR2, and VEGFR1 obtained using the methods of Example 5 and sequenced reads obtained using bulk ChIP-seq were analyzed. These data showed that the methods of an embodiment of the invention show less noise than shown by the bulk ChIP-seq method. These data also showed overlap of peaks derived from bulk ChIP-seq and the method of an embodiment of the invention in the locations of known active regions in the chromosomes. Peaks derived from the bulk ChIP-seq method are aggregates of many DNA fragments from individual cells. One cell generates one or two sequenced reads (in single-end read mode with high-throughput sequencers). Therefore, one broad peak in bulk ChIP-seq would be divided into a few sharp peaks in single-cell epigenome analysis. These figures show the broad band of bulk ChIP-seq splitting into several sharp peaks in the method of an embodiment of the invention.

Regions of chromosomes corresponding to epithelial cell markers Keratin 5; Keratin 8, Keratin 14; Keratin 17; scgb1a1; and N-cadherin obtained using the methods of Example 5 and sequenced reads obtained using bulk ChIP-seq were analyzed. Keratin 5 is a myoepithelial cell marker. Peak patterns in the Keratin 5 region showed very small peaks throughout the region, regardless of the system used for sequencing. Keratin 8 is a mammary epithelial cell marker. Peak patterns in the Keratin 8 region obtained using the methods of Example 5 showed one large peak and some peaks spread out through the region. Peak patterns obtained using bulk ChIP-seq showed mainly noise throughout the Keratin 8 region. Keratin 14 is a mammary and skin epithelial cell marker. Peak patterns in the Keratin 14 region obtained using the methods of Example 5 showed a few small peaks spread throughout the region. Peak patterns obtained using bulk ChIP-seq showed mainly noise throughout the Keratin 14 region. Keratin 17 is a mammary epithelial cell marker. Peak patterns in the Keratin 17 region obtained using the methods of Example 5 showed a few small peaks spread throughout the region. Peak patterns obtained using bulk ChIP-seq showed mainly noise throughout the Keratin 17 region. Scgb1a1 is a secretory epithelial cell marker. Peak patterns in the Scgb1a1 region obtained using the methods of Example 5 showed two localized peaks. Peak patterns obtained using bulk ChIP-seq showed two peaks at a different position, and noise throughout the Scgb1a1 region. N-cadherin is an epithelial-mesenchymal transition marker. Peak patterns in the N-cadherin region obtained using the methods of Example 5 and using bulk ChIP-seq showed many peaks throughout the N-cadherin region.

Regions of chromosomes corresponding to hepatocyte markers albumin and α-fetoglobulin, cytochrome P450 (1a1), and cytochrome P450 (1b1) were analyzed. Regions of chromosomes corresponding to immune cell markers CD3d & CD3g, CD3e, CD4, CD8a, and CD19 were also analyzed. Regions of chromosomes corresponding to muscle cell markers myoglobin Dl, myoglobin G, and Pax7 were analyzed. Regions of chromosomes corresponding to neural stem/progenitor cell markers GFAP, and nestin were analyzed. Regions of chromosomes corresponding to embryonic stem cell markers Oct4, Sox2, Klf4, and c-myc were also analyzed. The regions in these chromosomes did not appear to show peaks specific for any of these genes.

The results demonstrate that the methods of an embodiment of the invention are useful for sequencing genomic DNA in single cells. The results show that the methods of an embodiment of the invention preserve the spacing between nucleosomes when sequencing the genomic DNA. The results show that the methods of an embodiment of the invention result in peak patterns with less noise than those obtained when using bulk ChIP-seq. The methods of an embodiment of the invention produce peak patterns allowing for the identification of known active promoters, cell markers, and inactive regions.

This example demonstrates that it is possible to distinguish between active chromatin regions and inactive chromatin regions in paraformaldehyde fixed single cells using the series of reactions depicted in FIGS. 5A-5I and described in Example 5. Clinical samples are preserved using formaldehyde, without anchoring the cellular proteins using the nano-scale scaffold of an embodiment of the invention. These results suggest that nuclei or single cells isolated from clinical samples may be analyzed using the methods described in Example 5.

These results demonstrate that the methods of an embodiment of the invention produce a polyacrylamide nano-scaffold that anchors cellular components inside single cells. The polyacrylamide nano-scale scaffold preserves cellular proteins and genomic DNA in their location even after repeated experiments. This polyacrylamide nano-scale scaffold allows access of antibodies to these cellular components. This polyacrylamide nano-scale scaffold allows proteins to remain inside the cells even after multiple heating/cooling cycles, creating a re-usable single cell. The polyacrylamide nano-scaffold of an embodiment of the invention is degradable, allowing recovery of genetic DNA after epigenetic analysis. These results demonstrate that the methods of an embodiment of the invention allow for the genomic, epigenomic, and transcriptomic analysis of clinical samples preserved using formaldehyde.

Example 9

This example demonstrates that re-usable single cells obtained using the methods of an embodiment of the invention reduced positive and negative bias observed in conventional chromatin immunoprecipitation.

In this example, a comparative evaluation of structural bias in conventional chromatin immunoprecipitation (ChIP) and re-usable single cell analysis was performed. FIG. 8A, Bar #1 (left) represents the input control of bulk ChIP in K562 cells (data from Encyclopedia of DNA Elements, ENCODE project). Bar #2 represents the PFA-fixed single-cell: a K562 single-cell fixed with 4% Para-Formaldehyde, quenched the PFA with glycine, and embedded in polyacrylamide scaffold without protein anchoring. Bar #3 represents a re-usable single cell: a K562 single cell treated with 28% acrylamide and 4% PFA, and then anchored into polyacrylamide scaffold. Bar #4 represents reference heterochromatin/euchromatin regions in K562 cells (right). The regions of heterochromatin and euchromatin were determined by the ENCODE project using ChromHMM (Chromatin state discovery and characterization using a multivariate Hidden Markov Model). In the PFA-fixed single cell and in the re-usable single cell, distribution of mapped reads derived from control IgG is shown as an indicator of structural bias.

As shown in FIGS. 8B-8C, re-usable single-cell reduced negative bias in heterochromatin regions in comparison with bulk ChIP-seq. The left panel (FIG. 8B) shows that the number of single-cell reads overlapped with H3K27me3 peaks of bulk ChIP-seq. A non-fixed single cell is a single live cell which is embedded into a polyacrylamide scaffold without anchoring proteins and DNA to the polyacrylamide scaffold. In the right panel (FIG. 8C), bulk ChIP-seq showed that 16.03% of reads from the input control were non-specifically detected in identified peaks of H3K27me3 (a heterochromatin marker, trimethylated lysine 27 of histone H3), which indicates the background level of bulk ChIP-seq estimated from H3K27me3 analysis. In the anti-H3K27me3 antibody, 18.98% of the reads were detected in the identified peaks. The difference between the input control and anti-H3K27me3 was small (16.03% and 18.98%), which meant that the signal/noise ratio in bulk ChIP-seq is poor in heterochromatin regions.

In a negative control "non fixed single cell," control IgG showed a background level (16.58%) similar to the background level of bulk ChIP-seq (FIG. 8B). The specific signal level of anti-H3K27me3 in the non-fixed single cell (11.67%) was less than the background level of control IgG. This indicated that 11.67% of reads were randomly detected in the peak regions. In contrast, in the re-usable single cell, the background level of control IgG was reduced to 4.44%, which was a marked improvement over the background level of bulk ChIP-seq (FIG. 8B). Specific reads of the re-usable single cell were 29.52%. This demonstrated that the level of specific reads was improved in comparison with bulk ChIP-seq and the non-fixed single cell.

As shown in FIGS. 8D and 8E, the re-usable single cell improved positive bias toward euchromatin regions in comparison with bulk ChIP-seq. The left panel (FIG. 8D) shows that a number of single cell reads overlapped with peaks of bulk ChIP-seq in the non-fixed single cell and the re-usable single cell. The right panel (FIG. 8E) shows a number of reads of bulk ChIP-seq in statistically identified peaks. In the right panel, bulk ChIP-seq shows that 5.44% of reads from the input control were non-specifically detected in identified peaks of H3K27ac (acetylated lysine 27 of histone H3). This indicated the background level of bulk ChIP-seq in the H3K27ac analysis. In the specific analysis with anti-H3K27ac, 17.70% of reads detected corresponded to identified peaks. The differences between the input control and the anti-H3K27ac antibody were larger than those detected in the heterochromatin regions shown in FIGS. 8B-8C. In the non-fixed single cell, the control IgG showed a 3.55% background level in this assay (FIG. 8D). Specific reads detected in anti-H3K27ac of the non-fixed single cell were close to the background level. In the re-usable single cell, the background was reduced to 1.45% (FIG. 8D). Specific reads were expanded to 7.47%. The specific reads of anti-H3K27ac in the re-usable single cell were lower than the specific reads level of bulk ChIP-seq. The reads derived from euchromatin regions were 74.62% in the input control of bulk ChIP-seq and 43.61% in the re-usable single cell (FIG. 8A). The reduced specific reads in the re-usable single cell (FIGS. 8D-8E) supports the normalization of the positive bias in euchromatin regions.

This example demonstrated that a re-usable single cell analyzed with methods described herein normalized the negative bias in heterochromatin regions and the positive bias in euchromatin regions. This feature of the re-usable single cell method is important for multiplexed epigenome analysis.

Example 10

This example demonstrates that re-usable single cells obtained using the methods of an embodiment of the invention may be re-used for repeating testing on the same cell multiple times.

As shown in FIGS. 9A-9F, experiments were repeated using the same 8 single cells. The final products were generated in repeated experiments (Round 1-Round 6) using the same single cells (Single cell IDs: 1-8). FIG. 9G shows the yield of double-stranded DNA in the repeated experiments using the same single cells (FIGS. 9A-9F). The products were analyzed by the MISEQ high-throughput sequencer (Illumina, San Diego, Calif.). It was confirmed that these products contained antibody barcodes of control IgG, anti-H3K27ac, and anti-H3K27me3.

Example 11

This example demonstrates that the re-usable single cells obtained using the methods of an embodiment of the invention allow for the simultaneous analysis of multiple epigenomic markers and transcriptome in the same single cell.

The epigenomic marks may be detected by barcoding antibodies that specifically recognize different epigenomic modifications, as shown in FIGS. 9A-9F, 9G, and 10. These figures indicate that the heterochromatin marker H3K27me3, the euchromatin marker H3K27ac, and the control IgG can be analyzed in the same single cell. In the bar graph of FIG. 10, the striped patterned portion of each bar shows the numbers of reads containing the DNA barcode of anti-H3K27me3 antibody. The diamond portion of each bar shows the number of reads containing the DNA barcode of anti-H3K27ac antibody. The black portion of each bar shows the number of reads containing the DNA barcode of control IgG in the non-fixed single cell, PFA-fixed single cell, and re-usable single cell. The read numbers of anti-H3K27me3, anti-H3K27ac, and control IgG were distinguishable. The ratio of read numbers of anti-H3K27me3, anti-H3K27ac and control IgG were similar in the negative control, i.e., the non-fixed single cell. The ratio of anti-H3K27me3 and anti-H3K27ac was increased in the PFA-fixed single cell and in the re-usable single cell compared to the non-fixed single cell. This indicated that the number of reads generated depended on the preservation of protein and DNA location by PFA-fixation or anchoring proteins and DNA to the polyacrylamide scaffold. In addition, the same single cells successfully generated DNA products using antibodies for identification of DNA methylation, DNA hydroxymethylation, heterochromatin protein 1, mediator complex subunit 1 protein, and RNA polymerase II (FIGS. 9A-9F and 9G). Shallow sequencing by a MISEQ high-throughput sequencer was completed.

Example 12

This example demonstrates that the re-usable single cells obtained using the methods of an embodiment of the invention provide experimental controls in the analysis of the same single cell.

As shown in FIGS. 8B-8E, 9G and 10, IgG was included in these experiment as a negative control. The IgG-derived products were distinguished from other products derived from other antibodies by antibody barcodes. The control IgG provided evidence for the distribution of non-specific reactions and their frequency across the whole genome. De novo peak calling (peak finding) was performed without data aggregation of single cells. In addition to the control IgG, non-fixed single cells were used as a negative control (FIG. 10). The non-fixed single cells were useful to evaluate the level of non-specific reactions that occurred without the association of protein to genomic DNA.

This example demonstrates that the single cells obtained according to embodiments of the invention provide true single-cell analysis, as two experimental controls, i.e., the "control IgG" and the "non-fixed single-cell control." These negative controls distinguish a true signal from noise at a single cell level, and thus allows statistical analysis without data aggregation from multiple single cells. Such a method allows detection of signals from a single cell, including cells that represent less than 5% of the population.

Example 13

This example demonstrates that the claimed methods are applicable to different cell types.

FIGS. 1-7 provide results derived from the MS1 mouse cell line. FIGS. 8-10 provide results derived from the human erythroleukemia K562 cell line. This indicates that the claimed methods are not restricted by species and cell type if specific antibodies are available.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

---

The invention claimed is:

1. An in vitro method for preparing a re-usable single cell or nucleus, said method comprising:
   a) suspending a cell or nucleus in a solution comprising acrylamide and paraformaldehyde (PFA) to produce a first suspension of the cell or nucleus;
   b) resuspending the cell or nucleus in a solution comprising acrylamide-bisacrylamide or acrylamide-N,N'-bis(acryloyl)cystamine to produce a second suspension of the cell or nucleus; and
   c) adding N,N,N',N'-tetramethylethylenediamine (TEMED) to the second suspension of the cell or nucleus to polymerize the acrylamide;
   wherein a polyacrylamide nano-scale scaffold, is formed around the single cell or nucleus.

2. The method of claim 1, further comprising placing the first suspension on ice.

3. The method of claim 1, further comprising forming the second suspension into droplets of the solution comprising the single cell or nucleus and acrylamide-bisacrylamide or acrylamide-N,N'-bis(acryloyl)cystamine.

4. The method of claim 1, wherein the solution comprises 1% to 6% acrylamide-bisacrylamide.

5. The method of claim 1, wherein the solution comprises 1% to 6% acrylamide-N,N'-bis(acryloyl)cystamine.

6. The method of claim 1, wherein the TEMED is in mineral oil.

7. An in vitro method for preparing re-usable single cells or nuclei, said method comprising:
a) isolating cells or nuclei;
b) suspending the cells or nuclei in a solution comprising acrylamide and paraformaldehyde (PFA) to produce a first suspension of the cells or nuclei;
c) resuspending the cells or nuclei in a solution comprising acrylamide-bisacrylamide or acrylamide-N,N'-bis(acryloyl)cystamine to produce a second suspension of the cells or nuclei; and
d) adding N,N,N',N'-tetramethylethylenediamine (TEMED) to the second suspension of the cells or nuclei to polymerize the acrylamide;
wherein a polyacrylamide nano-scale scaffold is formed around the single cell or nuclei.

8. The method of claim 7, further comprising forming the second suspension into droplets of the solution comprising the single cell or nuclei and acrylamide-bisacrylamide or acrylamide-N,N'-bis(acryloyl)cystamine.

9. The method of claim 7, wherein the solution comprises 1% to 6% acrylamide-bisacrylamide.

10. The method of claim 7, wherein the solution comprises 1% to 6% acrylamide-N,N'-bis(acryloyl)cystamine.

11. The method of claim 7, wherein the TEMED is in mineral oil.

12. A method for analyzing for modification in at least one of the genome, epigenome, or transcriptome in a single cell or nucleus, said method comprising:
a) preparing a re-usable single cell or nucleus by the method of claim 1; and
b) detecting a modification in at least one of the genome, epigenome, and transcriptome in the single cell or nucleus when compared to a control genome, epigenome, or transcriptome.

13. A method for determining the location of an epigenetic modification in the genome of a single cell or nucleus, said method comprising:
a) preparing a re-usable single cell or nucleus by the method of claim 1;
b) binding an antibody to the epigenetic modification on the genome; and
c) sequencing a portion of the genome of the single cell or nucleus comprising the epigenetic modification to determine the location of the epigenetic modification on the genome.

14. A method for determining the nucleic acid position of an epigenetic modification in the genome of a single cell or nucleus, said method comprising:
a) preparing a re-usable single cell or nucleus by the method of claim 1;
b) annealing to the genomic DNA in the single cell or nucleus a first oligonucleotide primer, wherein the first oligonucleotide primer comprises, in a 5' to 3' orientation, a first random nucleotide sequence and a first ligation sequence (R);
c) extending the sequence of the first random nucleotide sequence using a first DNA polymerase;
d) binding at least one tagged antibody to an epigenetic modification, wherein the antibody is tagged with a polynucleotide comprising, in a 5' to 3' orientation, a first polymerase chain reaction (PCR) amplification sequence, an RNA polymerase promoter sequence, a restriction enzyme site sequence, an antibody barcode sequence, and a second ligation sequence (L);
e) joining the second ligation sequence (L) to the first ligation sequence (R) using a ligation adapter and a DNA ligase to create a ligation product;
f) annealing a second oligonucleotide primer to the ligation product, wherein the second oligonucleotide primer comprises, in a 3' to 5' orientation, a second random nucleotide sequence, a cell barcode sequence, a restriction enzyme site sequence, and a second sequence for PCR amplification;
g) amplifying the ligation product with the annealed second oligonucleotide primer using multiple displacement amplification (MDA) to obtain an MDA-amplified DNA;
h) amplifying the MDA-amplified DNA using PCR, in vitro transcription, and reverse transcription to obtain an amplified genomic DNA fragment; and
i) sequencing the amplified genomic DNA fragment to determine the nucleic acid position of the epigenetic modification in the single cell or nucleus when compared to a control epigenome.

15. A method for analyzing for modification in at least one of the genome, epigenome, or transcriptome in a single cell or nucleus, said method comprising:
a) preparing a re-usable single cell or nucleus by the method of claim 7; and
b) detecting a modification in at least one of the genome, epigenome, and transcriptome in the single cell or nucleus when compared to a control genome, epigenome, or transcriptome.

16. A method for determining the location of an epigenetic modification in the genome of a single cell or nucleus, said method comprising:
a) preparing a re-usable single cell or nucleus by the method of claim 7;
b) binding an antibody to the epigenetic modification on the genome; and
c) sequencing a portion of the genome of the single cell or nucleus comprising the epigenetic modification to determine the location of the epigenetic modification on the genome.

17. A method for determining the nucleic acid position of an epigenetic modification in the genome of a single cell or nucleus, said method comprising:
a) preparing a re-usable single cell or nucleus by the method of claim 7;
b) annealing to the genomic DNA in the single cell or nucleus a first oligonucleotide primer; wherein the first oligonucleotide primer comprises, in a 5' to 3' orientation, a first random nucleotide sequence and a first ligation sequence (R);
c), extending the sequence of the first random nucleotide sequence using a first DNA polymerase;
d) binding at least one tagged antibody to an epigenetic modification; wherein the antibody is tagged with a polynucleotide comprising, in a 5' to 3' orientation, a first polymerase chain reaction (PCR) amplification sequence, an RNA polymerase promoter sequence, a restriction enzyme site sequence, an antibody barcode sequence, and a second ligation sequence (L);
e) joining the second ligation sequence (L) to the first ligation sequence (R) using a ligation adapter and a DNA ligase to create a ligation product;
f) annealing a second oligonucleotide primer to the ligation product, wherein the second oligonucleotide primer comprises, in a 3' to 5' orientation, a second random nucleotide sequence, a cell barcode sequence, a restriction enzyme site sequence, and a second sequence for PCR amplification;

g) amplifying the ligation product with the annealed second oligonucleotide primer using multiple displacement amplification (MDA) to obtain an MDA-amplified DNA;
h) amplifying the MDA-amplified DNA using PCR, in vitro transcription, and reverse transcription to obtain an amplified genomic DNA fragment; and
i) sequencing the amplified genomic DNA fragment to determine the nucleic acid position of the epigenetic modification in the single cell or nucleus when compared to a control epigenome.

18. A kit for preparing a re-usable single cell or nucleus comprising:
formaldehyde and an acrylamide monomer,
acrylamide-N,N,N',N'-bis(acryloyl)cystamine or acrylamide-bisacrylamide,
TEMED in mineral oil, and
instructions to create a scaffold to prepare a re-usable single cell or nucleus.

* * * * *